United States Patent
Braun et al.

(10) Patent No.: US 9,545,192 B2
(45) Date of Patent: Jan. 17, 2017

(54) SYSTEM AND METHOD FOR AUTOMATIC NAVIGATION OF A CAPSULE BASED ON IMAGE STREAM CAPTURED IN-VIVO

(71) Applicant: GIVEN IMAGING LTD., Yoqneam (IL)

(72) Inventors: Ori Braun, Palo Alto, CA (US); Yaniv Ben Zriham, Binyamina (IL); Elisha Rabinovitz, Haifa (IL); Tomer Carmeli, Alonei Abba (IL); Jeremy Pinchas Gerber, Netanya (IL)

(73) Assignee: GIVEN IMAGING LTD., Yoqneam (IL)

( * ) Notice: Subject to any disclaimer, the term of this patent is extended or adjusted under 35 U.S.C. 154(b) by 82 days.

(21) Appl. No.: 14/398,853

(22) PCT Filed: May 2, 2013

(86) PCT No.: PCT/IL2013/050372
§ 371 (c)(1),
(2) Date: Nov. 4, 2014

(87) PCT Pub. No.: WO2013/164826
PCT Pub. Date: Nov. 7, 2013

(65) Prior Publication Data
US 2015/0138329 A1    May 21, 2015

Related U.S. Application Data

(60) Provisional application No. 61/642,540, filed on May 4, 2012.

(51) Int. Cl.
*H04N 5/225* (2006.01)
*A61B 1/04* (2006.01)
(Continued)

(52) U.S. Cl.
CPC ............ *A61B 1/041* (2013.01); *A61B 1/0005* (2013.01); *A61B 1/00016* (2013.01);
(Continued)

(58) Field of Classification Search
CPC ............ H04N 2005/2255; H04N 7/183; G06K 2209/057; A61B 1/041; A61B 1/00016; A61B 5/073; A61B 5/6861
(Continued)

(56) References Cited

U.S. PATENT DOCUMENTS

| 3,909,792 A | 9/1975 | Harris et al. |
| 4,278,077 A | 7/1981 | Mizumoto |

(Continued)

FOREIGN PATENT DOCUMENTS

| JP | 57-45833 | 3/1982 |
| JP | 4-109927 | 4/1992 |

(Continued)

OTHER PUBLICATIONS

U.S. Appl. No. 13/314,273, filed Jun. 14, 2012, Semion Khait.
(Continued)

*Primary Examiner* — Jessica M Prince
*Assistant Examiner* — Kathleen Nguyen
(74) *Attorney, Agent, or Firm* — Pearl Cohen Zedek Latzer Baratz LLP

(57) ABSTRACT

Embodiments of the invention include a method and system for displaying an in vivo imaging procedure. The method includes receiving real-time image data captured by the capsule, and continuously generating an updated summarized color bar, said color bar comprising color strips and time scale marks. The color bar is calculated based on color values of received image data, and is updated continuously as new image data is received. The displayed time period is periodically updated, for example based on predetermined
(Continued)

fixed time intervals, based on varying time intervals, or based on an accumulated amount of received image data. Other methods of determining the periodic updates may be used.

18 Claims, 9 Drawing Sheets

(51) Int. Cl.
| | |
|---|---|
| A61B 5/00 | (2006.01) |
| A61B 1/00 | (2006.01) |
| A61B 5/07 | (2006.01) |
| H04N 7/18 | (2006.01) |
| H04N 9/04 | (2006.01) |

(52) U.S. Cl.
CPC .......... *A61B 1/00158* (2013.01); *A61B 5/073* (2013.01); *A61B 5/6861* (2013.01); *H04N 7/183* (2013.01); *H04N 9/045* (2013.01); *G06K 2209/057* (2013.01); *H04N 2005/2255* (2013.01)

(58) Field of Classification Search
USPC .......................................................... 348/71
See application file for complete search history.

(56) References Cited

U.S. PATENT DOCUMENTS

| | | | |
|---|---|---|---|
| 4,936,823 | A | 6/1990 | Colvin et al. |
| 5,333,244 | A | 7/1994 | Harashima |
| 5,392,072 | A | 2/1995 | Rodriguez et al. |
| 5,519,828 | A | 5/1996 | Rayner |
| 5,604,531 | A | 2/1997 | Iddan et al. |
| 5,697,384 | A | 12/1997 | Miyawaki et al. |
| 5,970,173 | A | 10/1999 | Lee et al. |
| 5,993,378 | A | 11/1999 | Lemelson |
| 6,097,399 | A | 8/2000 | Bhatt et al. |
| 6,188,403 | B1 | 2/2001 | Sacerdoti et al. |
| 6,222,547 | B1 | 4/2001 | Schwuttke et al. |
| 6,240,312 | B1 | 5/2001 | Alfano et al. |
| 6,335,736 | B1 | 1/2002 | Wagner et al. |
| 6,428,469 | B1 | 8/2002 | Iddan |
| 6,614,452 | B1 | 9/2003 | Cable |
| 6,709,387 | B1 | 3/2004 | Glukhovsky et al. |
| 7,009,634 | B2 | 3/2006 | Iddan et al. |
| 7,174,202 | B2 | 2/2007 | Bladen et al. |
| 7,200,253 | B2 | 4/2007 | Glukhovsky |
| 7,219,034 | B2 | 5/2007 | McGee et al. |
| 7,245,746 | B2 | 7/2007 | Bjaerum et al. |
| 7,694,320 | B1 | 4/2010 | Yeo et al. |
| 7,986,337 | B2 | 7/2011 | Davidson et al. |
| 2002/0103417 | A1 | 8/2002 | Gazdzinski |
| 2002/0171669 | A1 | 11/2002 | Meron |
| 2002/0193669 | A1 | 12/2002 | Glukhovsky |
| 2003/0063130 | A1 | 4/2003 | Barbieri et al. |
| 2003/0077223 | A1 | 4/2003 | Glukhovsky et al. |
| 2003/0114742 | A1* | 6/2003 | Lewkowicz ....... A61B 1/00147 600/407 |
| 2003/0167000 | A1 | 9/2003 | Mullick et al. |
| 2003/0208107 | A1 | 11/2003 | Refael |
| 2004/0066398 | A1 | 4/2004 | Dolimier et al. |
| 2004/0184639 | A1 | 9/2004 | Jackson et al. |
| 2004/0196287 | A1 | 10/2004 | Wong et al. |
| 2004/0225223 | A1 | 11/2004 | Honda et al. |
| 2004/0249291 | A1 | 12/2004 | Honda et al. |
| 2004/0257620 | A1 | 12/2004 | Loce et al. |
| 2005/0281446 | A1 | 12/2005 | Glukhovsky et al. |
| 2007/0060798 | A1* | 3/2007 | Krupnik ............ A61B 1/00045 600/300 |
| 2009/0023993 | A1 | 1/2009 | Davidson et al. |
| 2009/0040235 | A1* | 2/2009 | Matsuda ............ A61B 1/00045 345/619 |
| 2009/0048484 | A1 | 2/2009 | Swain et al. |
| 2010/0086286 | A1 | 4/2010 | Lee et al. |
| 2010/0185225 | A1* | 7/2010 | Albrecht ................ A61B 5/036 606/191 |
| 2011/0032259 | A1* | 2/2011 | Kim ...................... A61B 1/041 345/428 |
| 2011/0135170 | A1 | 6/2011 | Wang |
| 2011/0164126 | A1 | 7/2011 | Ambor et al. |
| 2011/0243523 | A1 | 10/2011 | Davidson et al. |
| 2011/0301497 | A1 | 12/2011 | Shachar et al. |

FOREIGN PATENT DOCUMENTS

| | | |
|---|---|---|
| JP | 2004-249291 | 9/2004 |
| JP | 2004/321603 | 11/2004 |
| JP | 2004/337596 | 11/2004 |
| WO | WO 00/58967 | 10/2000 |
| WO | WO 01/65995 | 3/2001 |
| WO | WO 02/10223 | 2/2002 |
| WO | WO 02/26103 | 4/2002 |
| WO | WO 2012/127469 | 9/2012 |

OTHER PUBLICATIONS

Frohlich, B.: "Exploring Geo-Scientific Data in Virtual Environments", ACM Proc.Conf. on Vis., Nov. 1999, pp. 169-173, Figs. 4-5.

Economides,M.J. et al.: "Advances in Production Engineering", Web, Sep. 11, 2003, http://pumpjack.tamu.edu/-valko/CV/ValkoPDF/CanadianInvPaper.pdf.

Nuntius, et al.:"Multimedia Technology, H.264-A New Technology for Video Compression", pp. 1-4.

Lewis, B, "The Utility of Capsule Endoscopy in Obscure Gastrointestinal Bleeding", Techniques in Gastrointestinal Endoscopy, vol. 5 No. 3 (Jul. 2003) pp. 115-120.

The Weather Channel, www.weather.com (web page printed on Mar. 2, 2011).

\* cited by examiner

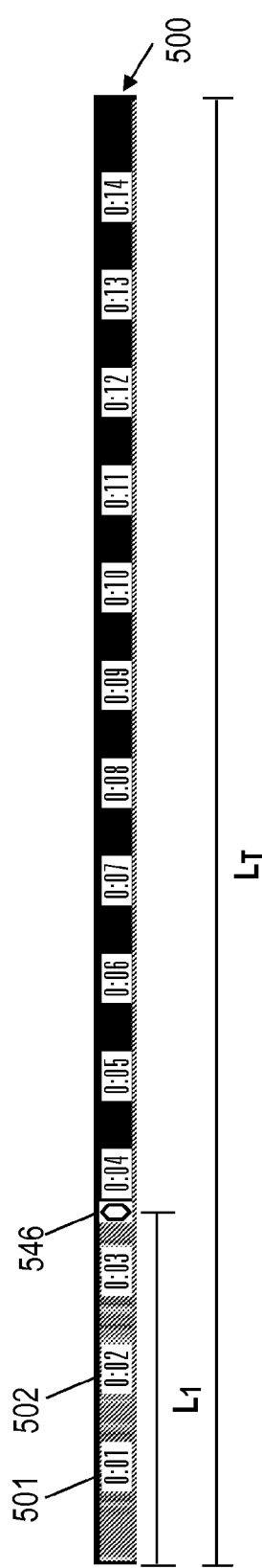
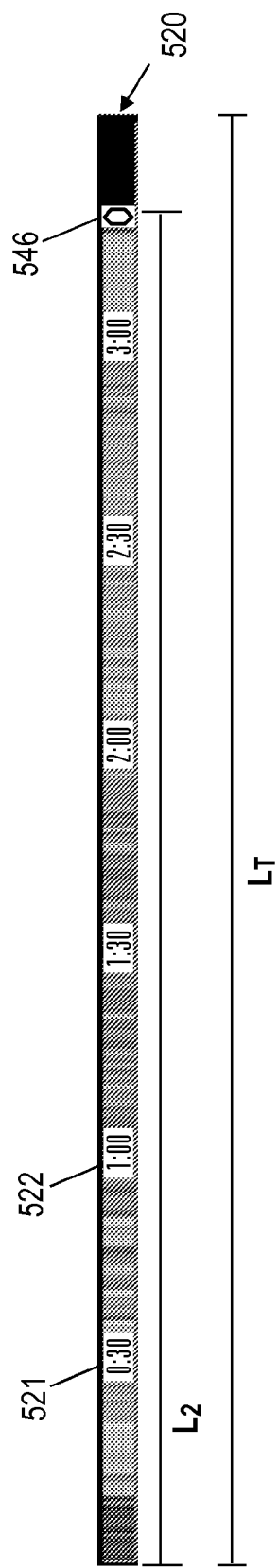
Fig. 5A
Fig. 5B

SYSTEM AND METHOD FOR AUTOMATIC NAVIGATION OF A CAPSULE BASED ON IMAGE STREAM CAPTURED IN-VIVO

CROSS-REFERENCE TO RELATED APPLICATIONS

This application is a National Phase Application of PCT International Application No. PCT/IL2013/050372, International Filing Date May 2, 2013, published Nov. 7, 2013 as International Publication No. WO 2013/164826, which in turn claims priority from U.S. Patent Application No. 61/642,540, filed May 4, 2012, all of which are incorporated herein by reference.

FIELD OF THE INVENTION

The present invention relates to systems and methods for automatic and semi-automatic navigation and display of an in vivo imaging capsule in a three-dimensional space. More specifically, the present invention relates to systems and methods for automatic and semi-automatic navigation of in vivo imaging capsule on data captured in-vivo.

BACKGROUND OF THE INVENTION

An in-vivo imaging system which is carried by an ingestible capsule may be used to image lumens within a patient's body, such as, for example, the gastrointestinal (GI) tract. The imaging system captures and transmits images of the passage or cavity to an external device, such as a recording device, while passing through the body. The images, when combined in sequence, may form a moving image stream of the passage.

As a passive system with no active maneuvering capability, once ingested, the capsule is carried throughout the entire GI system by natural peristalsis, while the orientation within the GI tract is random and uncontrollable. The capsule can neither be advanced forward to skip over regions that are not of interest, nor delayed or reoriented to provide a more in-depth view (e.g., closer examination) of suspected pathologies. The latter function is particularly important, as the mucosal surface of the GI tract is not smooth and often requires images of interest to be illuminated and visualized from various angles.

Magnetically maneuverable capsule endoscopy systems are disclosed in U.S. Patent Application Publication No. 20110301497 to Shachar et al., in U.S. patent application Ser. No. 13/314,273 to Khait et al., in PCT Application No. PCT/IL2012/050096 to Khait et al. and in PCT Application No. PCT/IL2012/000972 to Rabinovitz et al. Bladen et al. each of which is incorporated by reference herein in its entirety. A medical navigation apparatus for locating three dimensional position and orientation of a sensor by generating magnetic fields which are detected at the sensor in U.S. is disclosed in U.S. Pat. No. 7,174,202 to Bladen et al.

SUMMARY

Embodiments of the invention may include a method and system for displaying an in vivo imaging procedure. The method may include receiving real-time image data captured by the capsule, and continuously generating an updated summarized color bar, said color bar comprising color strips or other areas and time scale marks. The color bar may be calculated based on color values of received image data, and may be updated continuously as new image data is received.

The displayed time period may be periodically updated, for example based on predetermined fixed time intervals, based on varying time intervals, or based on an accumulated amount of received image data. Other methods of determining the periodic updates may be used.

Time intervals between the time scale marks on the color bar may also be updated periodically, for example upon every update of the displayed time period, as the imaging procedure progresses in time. An updated color bar comprising the updated time scale marks and updated color strips may be calculated in real time and displayed, for example using a combined display which may include the summarized color bar and an image stream of the real-time image data.

Real-time location data of the imaging device, such as a capsule, may be received, and the location data may indicate a position and orientation of the device in vivo. The location data and image data may be analyzed in real-time to determine a suggested direction for maneuvering the capsule. An indication of the suggested direction may be displayed along with a current image displayed from the image stream.

Periodic updates of time intervals between the time scale marks may be determined. In one embodiment, updated color strips may be calculated, for example by reducing the resolution of the displayed color strips. The periodic update of the displayed time period may be triggered, in some embodiments, based on the accumulated amount of received image data.

A system for displaying a real time in vivo imaging procedure may include a receiver for receiving real-time image data captured by an in vivo imaging device, and a processor to continuously generate an updated summarized color bar. The displayed time period may be periodically updated, and time intervals between said time scale marks may be periodically updated as well, either separately or along with the updating of displayed time period. A display for displaying a combined display of the summarized color bar and an image stream may be provided.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein:

FIGS. 5A and 5B are examples of a color bar presentation of a real-time in vivo imaging procedure according to an example embodiment;

Figure 1:
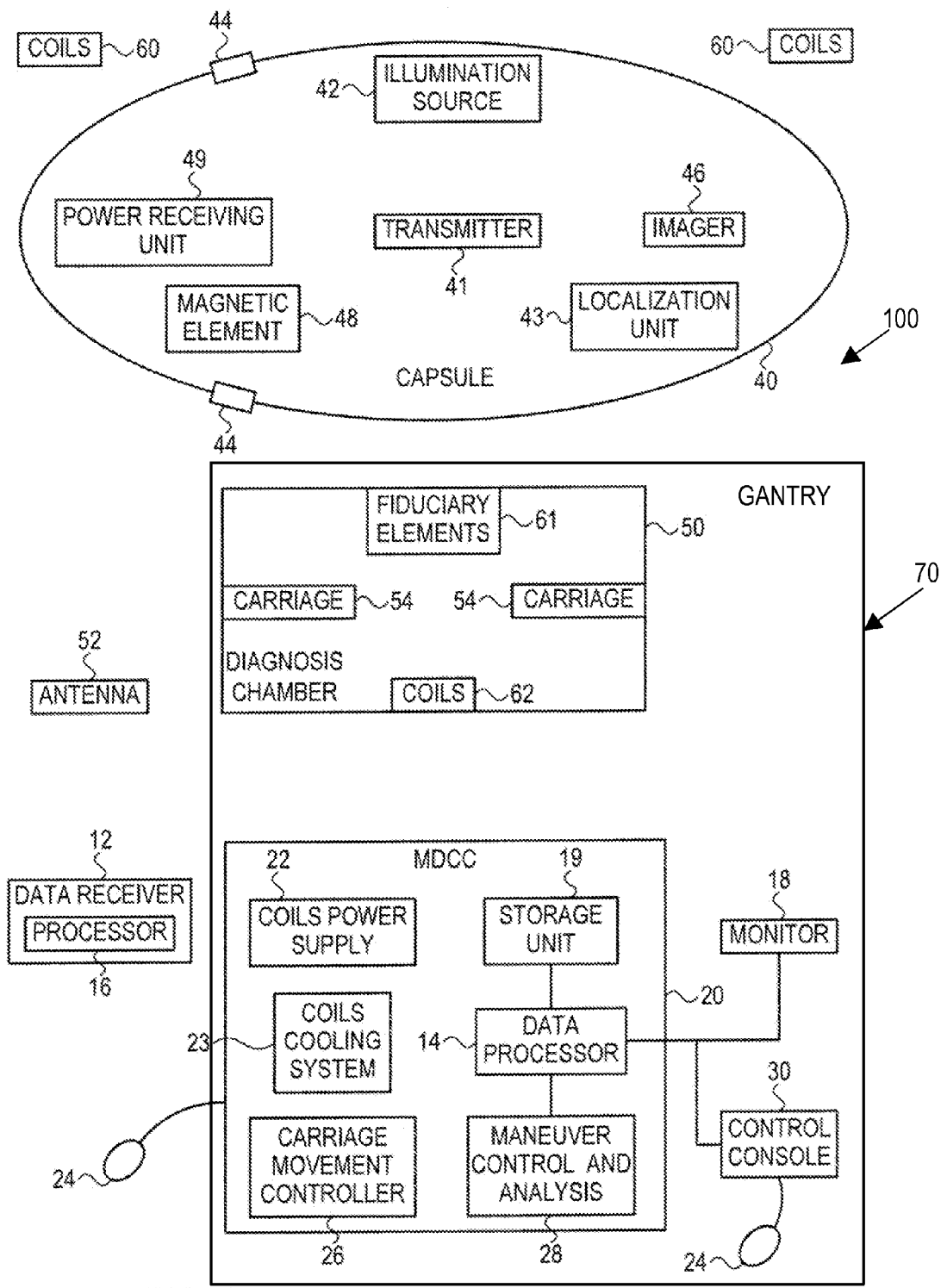
FIG. 1 is a schematic illustration of an in-vivo magnetically guided capsule endoscope system, according to an example embodiment.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise controllers, computers or processors selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus. It will be appreciated that a variety of programming languages may be used to implement the teachings of the invention as described herein.

Embodiments of the invention may include an article such as a non-transitory computer or processor readable medium, or a non-transitory computer or processor storage medium, such as for example a memory, a disk drive, or a USB flash memory, encoding, including or storing instructions, e.g., computer-executable instructions, which when executed by a processor or controller, carry out methods disclosed herein.

Some embodiments of the present invention are directed to a typically swallowable in-vivo device/capsule, such as a controllable swallowable capsule. In other embodiments, the in-vivo device need not be swallowable or controllable, and may have other shapes or configurations.

Reference is made to FIG. 1, which schematically illustrates an in-vivo magnetically guided capsule endoscope (MGCE) system 100 according to embodiments of the invention. According to some embodiments system 100 may comprise a capsule 40 having magnetic elements 48 or elements responsive to magnetic field, e.g. one permanent magnet or a set of permanent magnets or a combination of permanent magnets and metal discs or sheaths, a power receiving unit 49 and a capsule localization/positioning unit 43, which may include, e.g. coils, Hall Effect probes, gyro, acceleration meter, etc. Power receiving unit 49 may wirelessly receive power, for example, by accumulating energy electromagnetically. Capsule 40 may be surrounded by external magnetic field generators, e.g. coils 60 and coils 62.

System 100 may comprise a gantry 70, which may optionally include one or more of a patient diagnosis chamber 50, carriages 54, a Medical Displays and Control Console (MDCC) 20, data receiver 12, processor 16, monitor 18, control console 30 and input device(s) 24. Patient diagnosis chamber 50 may include an array of electromagnets (coils 62) arranged around a subject's torso on a standard patient table or carriages 54. Carriages 54 may be installed on rails located on or next to diagnosis chamber 50 and may slide in and out of diagnosis chamber 50. In some embodiments, carriages 54 may be fixed, and may enable diagnosis chamber 50 to slide along them. Diagnosis chamber 50 may also include an antenna or antenna array (antenna 52) to facilitate communication between capsule 40 and a data receiver 12, using a wireless communication such as radio frequency ("RF") communication, acoustic waves and/or ultrasound based communication. Antenna or antenna array 52 may be placed at various locations around chamber 50 or may be embedded within or below carriage 54.

Capsule 40 may be a swallowable in-vivo capsule, but other sorts of devices or suitable implementations may be used. In an example embodiment, capsule 40 may communicate with an external receiving and display system to provide display of data, control capability, or other functions. Power to capsule 40 may be provided, for example, by an internal battery, and/or by any device or circuit capable of picking up power, like coils responsive either to magnetic fields or to an RF transmission or any other wireless receiving system. Other embodiments may have other configurations and capabilities.

Capsule 40 may include an imager 46 for capturing images, an illumination source 42 for illuminating the body lumen, and an electronic circuitry and transmitter 41 to control the capsule functionalities such as transmitting image data and additional data to data receiver 12. Electronic circuitry and transmitter 41 may include, for example, an input-output ("I/O") interface/device, one or more controllers and a receiver. The receiver may be used, for example, to receive control information (e.g., to change a mode of operation, to change the value of a parameter, etc.), various messages. An optical system, including, for example, lenses or mirrors, may be used to focus reflected light onto imager 46.

Data receiver 12, preferably including a processor 16, may receive data from capsule 40. Processor 16 may be, for example, a DSP or any other real time processor or controller. In some embodiments, data receiver 12 may include a storage unit for storing the received data, while in other embodiments the data may not be stored in the receiver, and may either be transmitted or transferred to another storage unit or may not be stored at all. Processor 16 of data receiver 12 may calculate the location parameters of capsule 40, may perform methods as described herein, and may be responsible for other communication tasks such as sending the data to a regulator of diagnosis chamber 50 and to the physician display station.

According to one embodiment of the invention, system 100 may include a control unit, which is referred to herein as a Medical Displays and Control Console (MDCC) 20, for receiving the stream of images and location data from data receiver 12, processing the images' stream and location data and displaying the stream of images (or individual images) and the location data (and optionally additional information) to the physician. An input device 24 may be operationally connected to MDCC 20, and may be used to receive input of destination data for capsule 40 from a user (e.g., input device 24 may be or include a joystick, a pointing device or mouse, a keyboard, touch screen, stylus, light pen, trackball, or any other input device). The input data, or a modified or processed version thereof, may be sent to the regulator of diagnosis chamber 50 in order for it to facilitate generation of maneuvering commands. MDCC 20 may include a data processor 14, a storage unit 19 for storing, for example, data processed by data processor 14, and one or more monitors such as image monitor 18, which may be included as part of a personal computer or workstation which includes standard components such as a processor, a memory, a disk drive, and input-output devices, although alternate computer configurations are possible, and the system and method of the present invention may be implemented on various suitable computing systems.

Data processor 14 may include any standard data processor, such as a microprocessor, multiprocessor, accelerator board, or any other serial or parallel high performance data processor, and may perform methods as described herein. Image monitor 18 may be a computer screen, a plurality of screens, conventional video displays, or any other device capable of providing a video stream, images and/or other data.

Preferably, imager 46 is a suitable complementary metal-oxide-semiconductor (CMOS) camera, such as a "camera on a chip" type CMOS imager specified by Given Imaging Ltd. of Israel and designed by Micron Technology, Inc. In alternate embodiments, imager 46 may be another device, for example, a charge-coupled device (CCD). Illumination source 42 may be on include, for example, one or more light emitting diodes, or another suitable light source.

In operation (during the imaging process), imager 46 may capture images and send data representing the images (e.g., image data) to transmitter 41. At the same time, localization unit 43 may detect signals representing location data of capsule 40, and may output corresponding location data to transmitter 41. Transmitter 41 transmits the image data and the location or position data, or localization signals representing the location data, to data receiver 12 using, for example, electromagnetic radio waves. Localization signals or location data may be real-time localization or location data and may include position data of capsule 40 in the magnetic maneuvering space of MGCE system 100, and/or orientation data of capsule 40. The magnetic maneuvering space of MGCE system 100 may include the space between coils 60 (and/or 62) and carriage 54, in which the capsule can be maneuvered during the examination procedure. Based on the real-time location data, a position of capsule 40 may be determined, e.g. in relation to the patient and/or in relation to a fixed component of MGCE system 100 (such as carriage 54 or coils 60). Data receiver 12 may transfer the image data, location data and optionally other types of data, to data processor 14 that may store the transferred data in storage unit 19. In parallel, data receiver 12 may also transfer the data to the regulator of diagnosis chamber 50 to allow motion control of capsule 40. The data (e.g., image data and location data) collected and stored may be stored indefinitely, transferred to other locations, or manipulated or analyzed. A healthcare professional may use the images to diagnose pathological conditions of, for example, the GI tract, and, in addition, the system may provide information about the location of these pathologies. The data may be analyzed and used as input for the maneuver control and analysis unit 28 (which may be or include a processor, or which may use or be included in, for example, processor 14).

According to one embodiment, still images transmitted from capsule 40 as it traverses the GI tract may be combined consecutively to form a moving image stream and transmitted, sent or otherwise communicated to image monitor 18, which may either be connected to data processor 14 or remotely located in a central review station, where a healthcare professional may view the images as a live image stream or real time movie.

According to embodiments of the invention, capsule 40 may be shaped in a cylindrical manner; in other embodiments it may have an egg shape, a ball shape or any other round-type shape with no sharp edges.

Data processor 14 may analyze and edit the data, storage unit 19 may store raw data and/or processed data, and may provide the analyzed and edited data to, for example, a healthcare professional at a later time.

Capsule 40 may record images at a rate of, for example, two to forty images per second, other rates may be used. Capsule 40 may have a fixed or variable frame capture rate and/or transmission rate, fixed or variable field of view, and fixed or variable image magnification which may be changed automatically or by a command from a user. When imager 46 has a variable or adaptive frame rate (AFR) capability, imager 46 may switch back and forth between frame rates, for example, based on various parameters, such as capsule 40 speed, estimated location, similarity between consecutive images, or other criteria. The image recordation rate, the frame capture rate, the total number of images captured, the total number of images selected for the edited moving image, and the view time of the edited moving image, may each be fixed or varied.

Preferably, the image data recorded and transmitted by capsule 40 is digital color image data, although in alternate embodiments other image formats may be used. In an exemplary embodiment, each frame of image data includes 256 rows of 256 pixels each, and each pixel may have associated with it binary bytes for quantifying the pixel's color and brightness, according to known methods. Other numbers of pixels may be used, for example 320×320 pixels may be captured in an image frame, or high definition video resolution may be used, e.g. 1,280×720 pixels. For example, in each pixel, color may be represented by a mosaic of four sub-pixels, each sub-pixel corresponding to primary colors such as red, green, or blue (where one primary color is represented twice). In alternate embodiments, other formats such as hyper-spectral with multiple color filters may be used. The brightness of the overall pixel may be recorded by a one byte (i.e., 0-255) brightness value. According to one embodiment, images may be stored sequentially in data processor storage unit 19. The stored data may include one or more pixel properties, including color and brightness.

While, preferably, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

According to an embodiment of the invention, there is a maneuvering regulator (e.g., maneuver control and analysis unit 28). Maneuver control and analysis unit 28 may be a Programmable Logic Controller (PLC) or any other suitable commercial regulator known in the art. Maneuver control and analysis unit 28 may be a Modular PLC Controller which may include discreet input and output modules, a module for monitoring a cooling system, a thermocouple module for coil temperature monitoring, dedicated modules for power monitoring, etc.

A maneuvering regulator, for example maneuver control and analysis unit 28, may receive input data, such as location data detected by localization unit 43, and commands from control console 30, and generate/output, based on the input data and using dedicated algorithms, electrical current commands for coils 60 for producing magnetic fields for driving or maneuvering capsule 40 within the GI tract.

Coils 60 may induce controlled and regulated magnetic fields, for example as per the electrical current commands output/generated by maneuver control and analysis unit 28. The magnetic fields generated by coils 60 may interact with magnetic elements 48 to produce controlled translation and torque forces for moving, rotating and orienting capsule 40.

Moreover, the arrangement as described herein not only provides the forces and rotational torques to be exerted on the internal magnetic and conductive elements of a vessel such as the capsule to move, tilt and rotate in the body lumens, but also to follow, for example, an operator's or automatic computer generated direction and orientation commands (e.g., a "Go-To" command as described herein). According to some embodiments, the external magnetic fields need to overcome a force in the range of, for example, 10 grams or 100 grams.

According to some embodiments, pressure sensors may be installed in guided imaging capsule endoscope, such as capsule 40, in order to provide information regarding the pressure that the capsule exerts on a wall of a body lumen. In an alternative or a complementary embodiment, measurement of the pressure exerted by the capsule on a tissue of a wall of a body lumen may be inferred from the movement of the capsule when the resistance to the movement (if the capsule is driven into the tissue) is detected by the location system. For example if a certain amount of force is expected to move the capsule two centimeters (cm) away but the capsule actually moved only 1 cm, it may indicate unexpected resistance and thus may be interpreted as a movement of the capsule into a lumen wall or as the movement having a vector component directed towards the lumen wall.

In one embodiment, one or more pressure sensors 44 may be positioned on the housing of capsule 40, for example creating a structure similar to a ring near the capsule dome. Pressure sensors 44 may be located on the front of capsule 40, or on another part of the capsule in order to detect occurrences of high pressure acting on the capsule 40 during the medical examination, and/or to detect peristaltic waves and provide input to maneuver control and analysis unit 28 to increase counter forces to reduce such pressures. Such pressure sensors may be similar to, for example, General Electric's P161 sensor, which is a miniature silicon piezoresistive pressure sensor die.

According to a preferred embodiment, fiduciary marker or fiducial elements 61 (e.g., objects used in the field of view of an imaging system which appear in the image produced, for use as a point of reference or a measure) are attached to the subject to be examined, the subject lies on carriages 54 and his/her set of position coordinates relative to the bed is measured and used to calibrate the diagnosis chamber 50. Such setup/preparation procedure may take a short time, for example less than one minute. A capsule may be inserted into, or swallowed by the patient. The maneuvering magnetic fields are then activated and the capsule navigation may commence. A patient is expected to undergo the medical imaging procedure for a time period ranging from, for example, a few minutes for a short screening procedure (e.g. upper GI exam) up to two hours for a more lengthy GI tract examination. Typically, the system may work continuously or repeatedly during the day. Overlap may be possible, for example in the workstation level, for example during a current examination or imaging session, the results, or outcome, of a previous examination, or imaging session, may be handled (e.g., reviewed, further processed, stored or archived on the workstation or on another networked station).

According to embodiments of the present invention, a physician may view real-time movie images transmitted by the capsule endoscope in virtually real time, may watch the viewed organ or tissue concurrently from several perspectives, viewpoints and angles, and, optionally, use the visual feedback to navigate the capsule to a desired location, to position it in a desired orientation and to stop it—as may be needed. Real-time images, processing and display when discussed herein with the various aspects of embodiments of the invention may be contrasted with a system such as an offline system in which images are stored for later processing or display, and where information is displayed to a user significantly later than when received and processed. Real time may include substantially at the same time—e.g., if images, position information, or other information are received, processed, and displayed within fractions of a second, a user may perceive the operation to be real-time, even if there are some delays inherent in transmission and processing.

To facilitate the capabilities described herein, MDCC 20 provides a live or real-time video display of the organ or tissue of interest, as received by the optical system of the capsule endoscope along with schematic representation of the location and orientation of the capsule, for example on the same display screen, employing side areas next to the display of the organ/tissue.

One or more external elements may be used as reference points and assist in calculating the accurate movement of the capsule in the body lumen. External elements functioning as fiduciary markers 61 may be made of coils, for example, and may be connected by a wired or wireless connection to the workstation, for use as a point of reference in the system. Each fiduciary element 61 may produce a signal which may be processed in the workstation to determine the relative position of the capsule in the three-dimensional space, in relation to the fiduciary markers 61. The fiduciary markers 61 may be placed on the patient's body, for example external to the patient, and/or on the operation table or bed on which the patient is lying. In some embodiments, the fiduciary markers 61 may include wireless units which may constantly or repeatedly transmit positioning or location information, as part of the MGCE system 100. In some embodiments, the fiduciary markers 61 may include wired units which may be operationally connected to, for example, the workstation or a controller of the external magnetic field. The positioning information produced by the fiduciary markers 61 may be used to calculate the relative and/or absolute movement of the capsule in the body lumen, for example by subtracting the patient's movements (e.g. caused due to breathing, voluntary movement, heartbeat, etc.) from the absolute capsule movement.

Based on fiduciary markers 61, a set of coordinates relative to the patient's body may be defined, and the capsule's location (including, for example, position and orientation) may be calculated in relation to this set of coordinates. The origin of the set of coordinates may be determined to be a fixed point, for example on the bed and not on the patient, in order to calculate the capsule's location in space relative to the fixed point. The calculated location of the capsule may be corrected, for example in real time, by subtracting the patient's movements (calculated according to the fiduciary markers 61) from the capsule's movements or path.

In some embodiments, the fiduciary markers 61 may be positioned in specific predetermined anatomical placements, such as substantially adjacent to the xiphoid process on the lower part of the sternum, or adjacent to the navel, in order to help locate an area which requires treatment. Positioning the fiduciary markers in predetermined placements on the patient's body may allow determining a location of a pathology (e.g. a lesion, a polyp, a tumor, bleeding, etc.) in a coordinate system which may be aligned with the patient's skeletal structure.

Figure 2A:
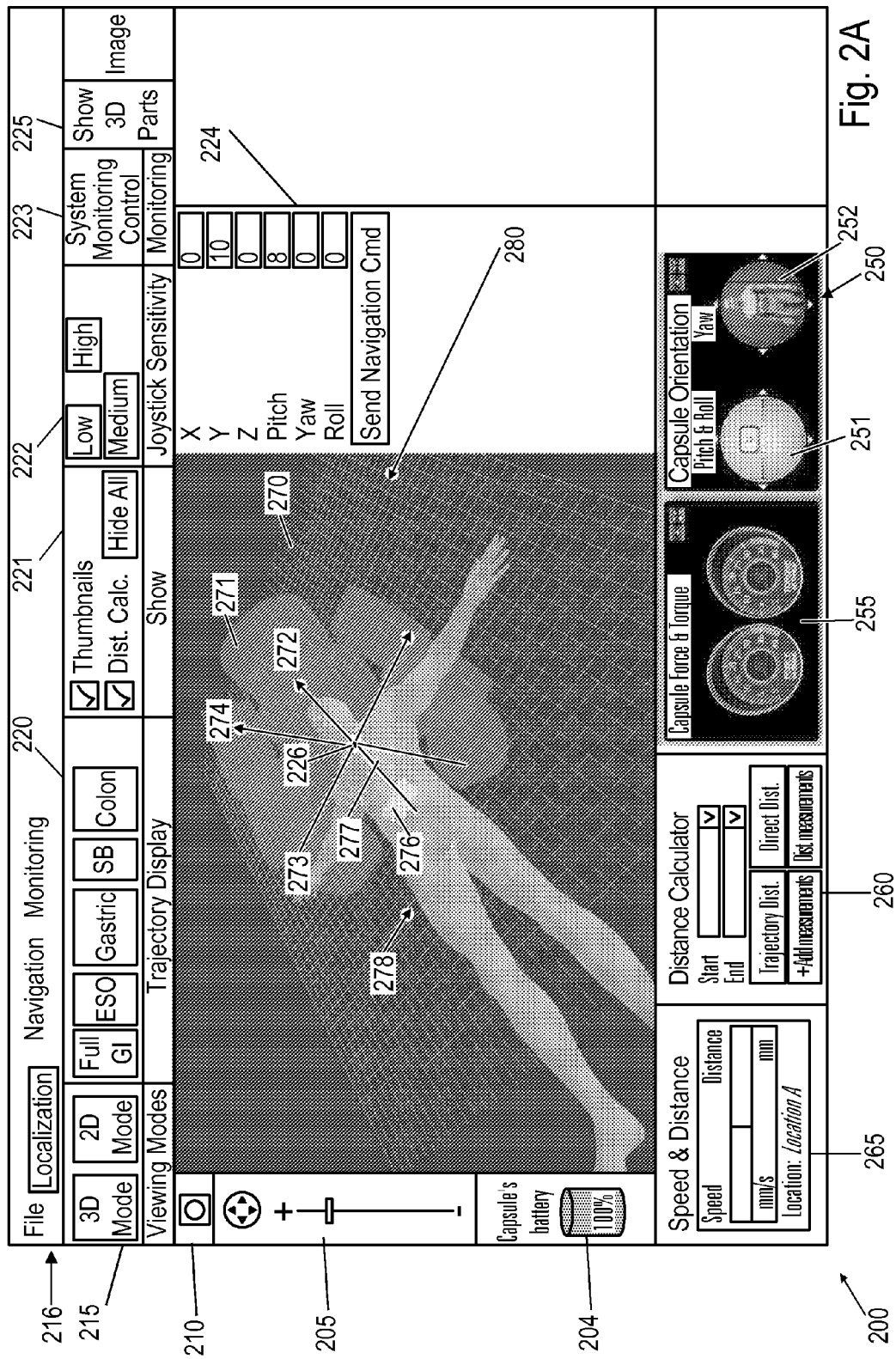
FIGS. 2A-2C illustrate graphic user interfaces for use of a physician during navigation of an in vivo capsule endoscope according to an example embodiment.

Reference is made now to FIG. 2A, which illustrates an exemplary graphic user interface 200 for the use of a physician during navigation of a capsule endoscope according to example embodiments. The display area of user interface 200 may be partitioned into multiple windows or subareas. Multiple tabs or other navigation or selection tools 216 may be provided to the user, each tab amalgamating a certain group of related functionalities or options, for example File, Localization, Navigation and Monitoring tabs. In FIG. 2A, the Localization tab is illustrated, along with a set of optional functionalities related to the display and control of the position and orientation of the maneuvered capsule.

Window 280 may display a model 278 of a human body or torso, which may represent the body of the patient undergoing an examination procedure. Model 278 may include shapes or outlines of organs relevant to the examination procedure, e.g. small bowel 276, esophagus 277, stomach, colon, etc. Other organs may be marked or indicated on model 278, e.g. according to the selected organs to be displayed (which may be chosen by a user via control bar 220). An arrangement of the magnetic coils 271 (e.g. 12 coils 60 and 62 of FIG. 1) for generating the maneuvering motion of capsule 40 may be indicated in the space around model 278.

Model 278 may be generated using a predetermined size and/or body proportion, or may be generated according to patient's dimensions which may be for example input by the user. Model 278 may be updated or altered, for example during the real-time imaging procedure, according to calculated dimensions of in vivo organs which may be estimated or computed based on image and/or position data received as the procedure is performed.

Figure 4B:
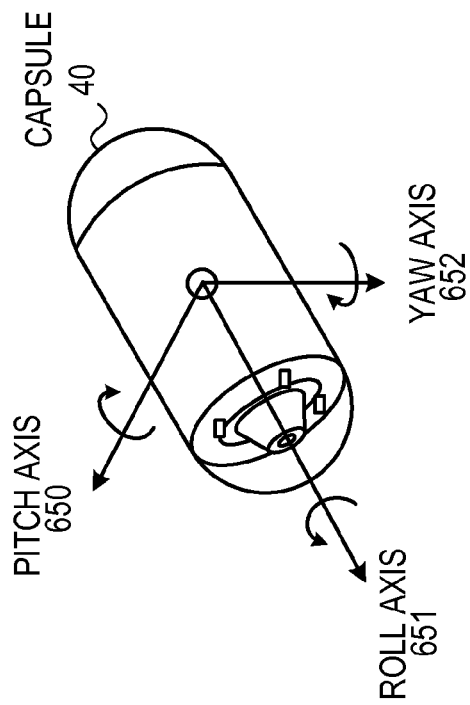
FIG. 4B illustrates a coordinate system of capsule orientation according to an example embodiment of the invention.
Figure 4A:
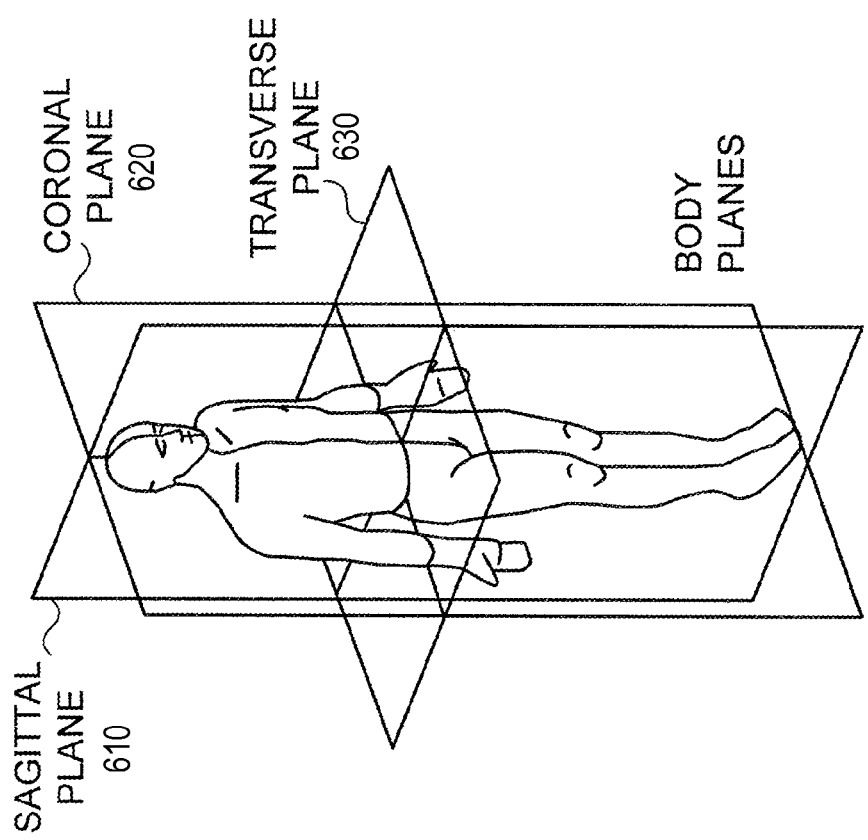
FIG. 4A illustrates a coordinate system of body planes according to an example embodiment of the invention.

Reference is now made to FIG. 4A, which illustrates the sagittal plane 610, coronal plane 620 and transverse plane 630 in relation to a patient's body (or in relation to a model 278). Grid 270 may indicate the surface on which the patient is lying, e.g. surface of carriage 54 shown in FIG. 1, and may be determined as the coronal plane 620 (or parallel to it). The position of capsule 40 may be represented by point 226, and a calculated or estimated real-time position and orientation information pertaining to the capsule at the time the currently displayed image was captured, may be schematically displayed in relation to model 278.

A predetermined gantry coordinate system indicated by e.g. reference axes 272, 273 and 274 may be displayed in relation to capsule 40 when it is in vivo. Point 226, connecting the reference axes of the coordinate system, may indicate the location of capsule 40 within the magnetic maneuvering space. In one embodiment, the axes 272, 273 and 274 may indicate the movement of the capsule 40 in relation to a coordinate system, for example, in relation to the patient's body or to the magnetic maneuvering system (e.g. coils 271 or carriage 54). For example, axis 272 may be located on the plane of grid 270 or parallel to it, and aligned with the longitudinal axis of model 278 (e.g. arrow 272 may be parallel to the line adjoining sagittal plane 610 and coronal plane 620). Axis 273 may be located on grid 270 (or parallel to it) and aligned with the transverse plane 630 of model 278 (e.g. arrow 273 may be parallel to the line adjoining transverse plane 630 and coronal plane 620). Axis 274 may be located perpendicular to grid 270 (e.g. may be parallel to the line adjoining transverse plane 630 and sagittal plane 610).

Position of fiduciary markers 61 may also be displayed on window 280, e.g. according to (or in relation to) their actual placement around the patient's body. The position of fiduciary markers 61 may define a patient coordinate system. For example, the fiduciary markers 61 may be placed at predetermined positions on the patient's body (e.g. on the navel), and a patient coordinate system may be defined according to reference axes passing through at least a portion of fiduciary markers 61.

Referring to FIG. 2A, a viewing mode may be selected by the user, e.g. a two-dimensional viewing mode or a three-dimensional viewing mode, as indicated in control box 215. Such selections, and other selections discussed herein, may be made by for example a user input device 24 or other device (e.g., a mouse, keyboard, joystick, etc.). A two dimensional viewing mode may include, for example, display of the position of the capsule in three planes, e.g. in the sagittal, coronal and transverse planes of the patient's body shown in FIG. 4A. Control bar 220 may allow selection of one or more organs to be displayed on model 278. The user may select, for example, display of the esophagus, stomach, small bowel, colon, and/or a full GI model including, for example, the above-listed organs or other organs. Other displays may be used. For each displayed organ, the trajectory or curve of the capsule 40 passing through the organ may be displayed or hidden according to the user selection. Control box 221 allows hiding or showing thumbnails display (e.g., downsized or reduced sized or resolution images captured by capsule 40 and selected automatically by the system or manually by the user) and display of a distance calculator (window 260).

The sensitivity of the user input device 24 (e.g. joystick) may be adjusted in window 222. For example, the default setting may be determined to be high sensitivity to the user's movement of the joystick, however, medium or low sensitivity may be selected. Such configuration may be used, e.g., for a training mode or for inexperienced users. Window 223 displays monitoring panes of the system.

Figure 2B:
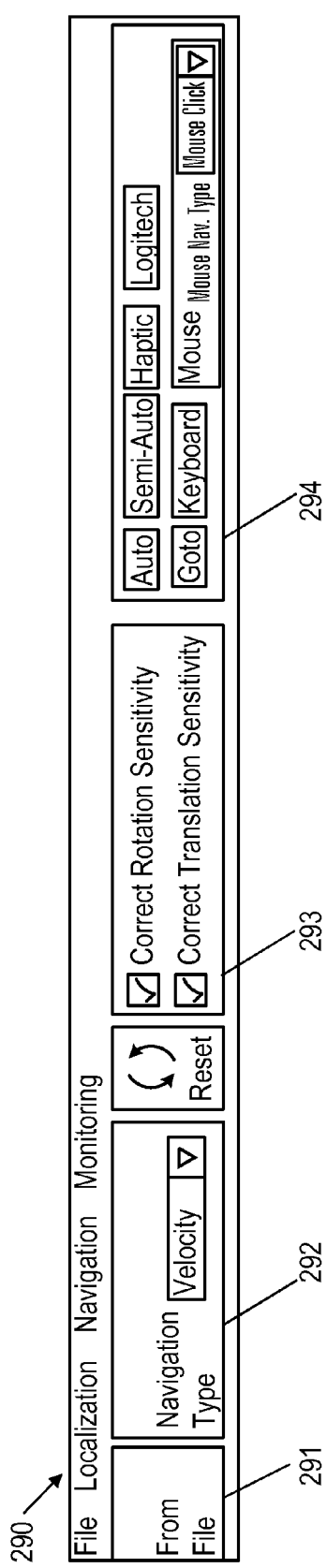
Figure 2C:
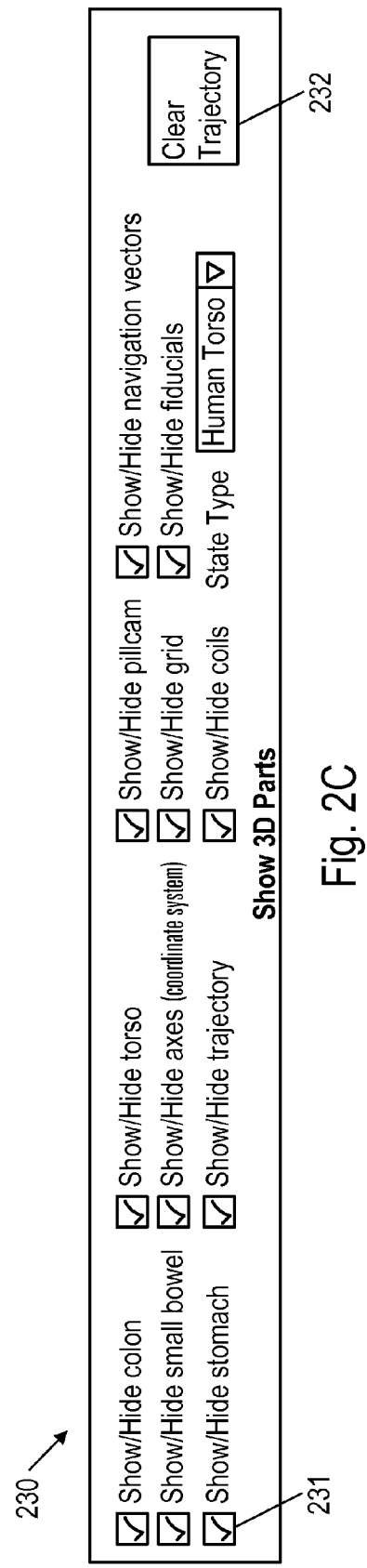

Button 225 includes options for displaying or hiding features which may be viewed in window 280, further detailed in FIG. 2C.

Different navigation methods may be applied to drive the capsule. According to some embodiments, the user (e.g.

physician) may control the capsule by selecting a spatial position and orientation for driving the capsule. If an area of interest is detected in a particular image captured by capsule 40, either automatically by image processing detectors or visually by the user, the area of interest in the image may be marked, and the user may use navigation controls, e.g. provided in control box 224. Detectors, such as a blood detector, an ulcer detector, a polyp detector, may be processes, such as software stored in memory and executed by a processor, such as processor 16.

In some embodiments, capsule 40 may be guided to the desired position by inputting parameters for a navigation command comprising, for example, spatial parameters relating to six degrees of freedom: the X, Y, and Z spatial coordinates of the desired position in the magnetic maneuvering space, and the pitch (lateral axis), yaw (vertical axis) and roll (longitudinal axis) orientation of capsule 40. The orientation axes of the capsule are shown in FIG. 4B: pitch axis 650, roll axis 651 and yaw axis 652. A navigation command may be sent, for example from control console 30 to a maneuver controller (e.g. to maneuver control and analysis unit 28), which may activate the external magnetic fields in order to drive the capsule to the desired position. The current capsule orientation may be displayed to the user, as shown for example in window 250, using a pitch and roll view 251 and a yaw view 252.

In one embodiment, the total force and torque acting on the imaging capsule may be continuously or periodically determined and/or measured during the procedure. When used herein, "continuous" or "continual" determining, measuring, calculating, updating, imaging, etc. may mean performing such actions or other actions on an ongoing basis, at repeated intervals, and may mean performing such actions with no gaps in time between actions, or may mean performing such actions periodically with some gaps in time between actions. The output or outcome typically is presented to the user as an ongoing repeated action. For example, the force may be calculated according to sensed pressure information, which may be received e.g. from pressure sensors 44 and/or according to voltage, current and/or magnetic field information. The pressure sensors 44 may provide indication of the total forces (e.g., pressure from tissue walls and magnetic forces) which are acting on the capsule. When the capsule is maneuvered into a tissue wall, the pressure sensors 44 may indicate that the pressure on the capsule exceeds a safety threshold, and may be dangerous for the patient (e.g., may cause rupture of the intestinal walls). In such cases, the magnetic maneuvering force may be automatically shut off or lowered, for example to a minimal intensity, thus preventing accidental damage to the tissue walls.

Signals from pressure sensors may be received by a receiving system, and a controller or processor (e.g., controller or processor 14, 16, or unit 28, or another unit or combination of units) may determine that the amount of pressure acting on the capsule housing exceeds a certain threshold. As a result, the controller may automatically change or recalculate the direction for maneuvering the capsule. The force and torque acting on the capsule may be continuously or periodically calculated in real-time during the maneuvering procedure, and continuously displayed and updated or altered in window 255. In some embodiments, a force-feedback device such as a force-feedback joystick may be used, allowing the user to feel the pressure exerted on the capsule by the tissue walls, and facilitating the manual navigation of the capsule.

In order to calculate the force and/or torque exerted on the capsule, the following steps may be used (other or different steps may be used):
(i) Determine the force that the external magnetic field activates on the capsule;
(ii) Estimate the expected motion of the capsule caused as a result of the external magnetic field;
(iii) Estimate the expected resistance force working on the capsule;
(iv) Determine actual movement of the capsule after the external field activation;
(v) Calculate the difference between the expected displacement of the capsule and the actual displacement.

Calculation of the resistance force may be based on a model of the resistance that the tissue causes on the capsule. The resistance model may be different per organ, for example, if the capsule is in the small bowel, the resistance model may be a first function $F_1$, while if the capsule is in the stomach, a different function $F_2$ may be applicable. Calculation of the force acting on the capsule may be performed, for example, by multiplying the magnetic field gradient acting on the capsule by the magnetic moment of the capsule.

Monitor 18 may be operable to continuously, repeatedly or periodically display representation of the position and orientation of capsule 40 as it traverses the GI tract. Continuous position and orientation data of capsule 40 may be received (e.g. from positioning or localization unit 43, or sensed by external magnetic fields) and processed, e.g. by processing unit 14 or by another processor or controller. A trajectory of the capsule may be calculated, e.g. a two-dimensional or three-dimensional path or curve. The trajectory may indicate the path in which capsule 40 passed during its traverse of the GI tract, and its current position. The trajectory may be updated continuously or repeatedly, in real time (e.g., periodic intervals when a processor turns to the task), during the capsule maneuvering procedure, and as the procedure progresses in time. Based on the position and orientation data, an average or momentary speed of capsule 40 may be continuously or repeatedly calculated and presented to the user, e.g. via window 265.

As shown in window 260, a user may select two points, for example using a mouse, joystick, keyboard, touch screen, or other input device 24, and a trajectory distance or direct distance between the selected input points may be calculated and displayed to the user. The points may include, for example, landmarks, predetermined points, pathological candidates detected during the procedure, or points automatically or manually selected during the examination procedure. A direct distance (e.g. aerial distance or Euclidean distance) between the input points in the magnetic maneuvering space may be calculated. If the two input points are positioned on the capsule trajectory, the trajectory distance may be calculated (e.g., the distance traveled by capsule 40).

In some embodiments, not every position data point and/or orientation data point (received from localization unit 43 or from another positioning unit) may be added to the calculated capsule trajectory. In some embodiments, only data points which satisfy a certain predetermined condition may be used to calculate the capsule trajectory. For example, assuming a position data point $P_1$ was added to the trajectory, the next position data point $P_2$ may be added only if the Euclidean distance between $P_1$ to $P_2$ is larger than a predetermined threshold, e.g., 3 millimeters. In some embodiments, if the capsule sways back and forth in the same region for a certain period of time, the position points that include the back and forth movement between two points may not be included in the displayed trajectory. In another example, the points may be displayed on the trajectory, but may not be used for calculating the trajectory distance between two input points.

Window 204 may show a schematic indication of the status of the power source of capsule 40. The battery state may be received, for example sent from the capsule along with additional data, and an indication may be displayed to the user. The indication may alert a physician if the battery voltage level is low during the examination procedure. Window 205 includes a resizing control of displayed model 278. Model 278 may be zoomed in and out per user definition. Furthermore, model 278 may be rotated and turned, for example using an input device such as a mouse, by dragging the input device along window 280 to the desired position and angle of the model. Model 278 may be rotated in any direction on the display, in order to demonstrate the model from a plurality of perspectives.

Maneuvering indicator 210 may indicate a state or condition of the maneuvering control loop of the system. For example, when maneuvering indicator 210 is green, the maneuvering functionality may be working properly, e.g. receiving commands from a user via control console 30 and applying the commands to the external magnetic fields to generate the desired capsule movement. If the maneuvering control loop fails, maneuvering indicator 210 may, for example, be illuminated in red color, flash or provide another indication that a problem in the maneuvering control loop is detected. Maneuvering indicator 210 may receive status indications from different system components, e.g. coils 60 or 62, carriage 54, fiduciary markers 61, maneuvering regulator 28, coils power supply 22, coils cooling system 23, etc. If one or more components of the system fail, maneuvering indicator 210 may indicate that the system is not fully functioning.

Reference is now made to FIG. 2B, which shows an exemplary graphic user interface according to an embodiment of the present invention. A Navigation control tab 290 may be used, for example in addition to other functional tabs in the user interface. The navigation tab 290 may combine functionalities related to the navigation and maneuvering of a magnetically maneuverable capsule 40.

In some embodiments, different motion patterns may be applied to the movement of capsule 40 in vivo. Button 291 may allow a user to apply a preconfigured movement type on the capsule's navigation pattern. For example, a capsule 40 may be caused to move in a spiral pattern, somersault movement or a wiggling pattern, instead of or in addition to a straight or direct movement from one coordinate in space to another. In one example, magnetic maneuvering force may be activated on the capsule by coils 60. If the capsule remain static or substantially static as a result of the activated force, it may be determined that the capsule is trapped or caught, for example in a certain portion of the GI tract (e.g. cecum or in a narrowed or obstructed portion of the intestinal lumen), or in a tissue fold. The preconfigured motion pattern may release a capsule which may be momentarily trapped, or if it drags the tissue walls along when it moves.

The imaging procedure may be performed with a single-head imaging capsule (e.g. a single imaging system) or a capsule with multiple imaging systems (two or more). If the capsule comprises a single imaging system, its progress in the GI tract may be oriented in a forward-facing direction (e.g., the imaging system faces the direction of normal progress through the GI tract, from mouth to anus) or a backward-facing direction (e.g. the imaging system faces opposite the direction of normal progress through the GI tract). If it is detected that the capsule is oriented in a backward-facing direction, a somersault movement type may be initiated. The somersault motion may cause the capsule to flip to a correct orientation. The somersault motion may be similar to embodiments described, for example, in U.S. Patent Application Publication Number 20090048484 to Swain et al., incorporated by reference herein in its entirety.

A capsule navigation command form may be selected by the user, and may be changed during the imaging procedure. For example, button 292 may allow selecting among various navigation methods, e.g. navigation applied according to the desired capsule velocity, or navigation applied according to desired orientation and spatial coordinates of the capsule. Other navigation methods may be selected and applied.

A user may input navigation or maneuvering commands of the capsule according to different coordinate systems. For example, the user may provide the maneuvering commands according to a patient coordinate system and/or according to a gantry coordinate system. A patient coordinate system may be defined as a set of reference axes which are positioned in a fixed placement in relation the patient's body. A gantry coordinate system may be defined as a set of reference axes which are positioned in a fixed placement in relation to a certain component of gantry 70, e.g. to carriage 54 or coils 60. A set of coordinates provided in the patient coordinate system may be transformed to a set of coordinates in the gantry coordinate system, and vice versa. The transformation of the coordinates may be performed, for example, based on the position of the patient's body relative to the gantry coordinate system. The patient's position may be determined based on fiduciary markers 61. A user may select, in control bar 293, automatic correction of rotation sensitivity and translation sensitivity. The correction may be performed automatically by a processing unit, e.g. processor 14.

Various input devices 24 may be used to control the maneuverable imaging capsule. A user may select a preferred input device in control bar 294, and per selected input device, a navigation method may be selected. Optional input devices include, but are not limited to, mouse, keyboard, and different types of joysticks (e.g. a Logitech™ joystick, Haptic, etc.). For example, if a mouse is used as the input device, the navigation may be manual navigation (e.g. capsule receives navigation commands sent from the mouse and translated to coordinates in space or to capsule velocity, according to the navigation command form). Manual mouse navigation may be applied in different methods, for example the user may be required to click on the currently displayed real-time image, on the next position that the capsule should be maneuvered to. In some embodiments, the user may simply hover with the mouse over the image, in the direction in which the capsule should be driven. Maneuver control and analysis unit 28 may translate the coordinates of the mouse cursor in the image to spatial coordinates, and may cause the capsule to move in the appropriate direction.

In some embodiments, the navigation may be automatic navigation, e.g. an automatic navigation control unit may determine the capsule's next position or desired movement, and may automatically send the necessary navigation command to maneuvering control and analysis unit 28. An example of an image-based automatic navigation control unit is described in PCT Patent Application PCT/IL2011/000972 to Rabinovitz et al., assigned to the common assignee of the present application and incorporated by reference herein in its entirety.

In some embodiments, a semi-automatic navigation control scheme may be applied to the capsule. For example, a lumen hole region may be detected in the images, and a suggested or recommended capsule motion directed to the center of the identified lumen hole may be displayed, for example in maneuvering window 280. An arrow, pointer or other indicator or indication indicating the suggested direction or motion may be displayed or overlaid on a current image displayed from the image stream. The suggested motion may be displayed, for example, as an arrow or pointer pointing to the suggested region. A suggested capsule orientation may also be displayed, e.g. in the same window or separately. Several navigation and/or display methods may be combined in a single procedure or applied in parallel. The suggested or recommended direction may be used by a medical practitioner. For example, a "Go-To" command may be issued by a medical practitioner, or a manual navigation command may be issued by inputting desired coordinates via input device 24.

A Go-To command is a navigation command issued to the capsule, to maneuver the capsule to a desired spatial position. The Go-To command may be applied, for example, by sending specific position coordinates to maneuver control and analysis unit 28, which may cause the capsule to reach the desired position. In some embodiments, the user may select a previously captured image or thumbnail, and use it as the input of the Go-To command. In such occurrence, maneuver control and analysis unit 28 may first determine coordinates of the spatial position in which the selected image or thumbnail was captured, and then produce a navigation command to drive the capsule to the desired coordinates.

Reference is now made to FIG. 2C, which shows an exemplary graphic user interface according to an embodiment of the present invention. A display control bar 230 may be configured according to the user's preference. Features or items which are relevant to the navigation of capsule 40 may be displayed or hidden, by checking a checkbox 231 for example. Other interface options are possible for addition or removal of items from the graphic display. For example, different portions in window 280 may be displayed or hidden (e.g. colon, small bowel, stomach, torso 278). Similarly, coordinate system axes 272, 273 and 274, coils 271, capsule representation 226, trajectory, grid 270, fiduciary markers 61 and the navigation vectors may be displayed or hidden from view according to the selection of the user. The trajectory path which the capsule passes during the procedure may be cleared or maintained using button 232.

Figure 3A:
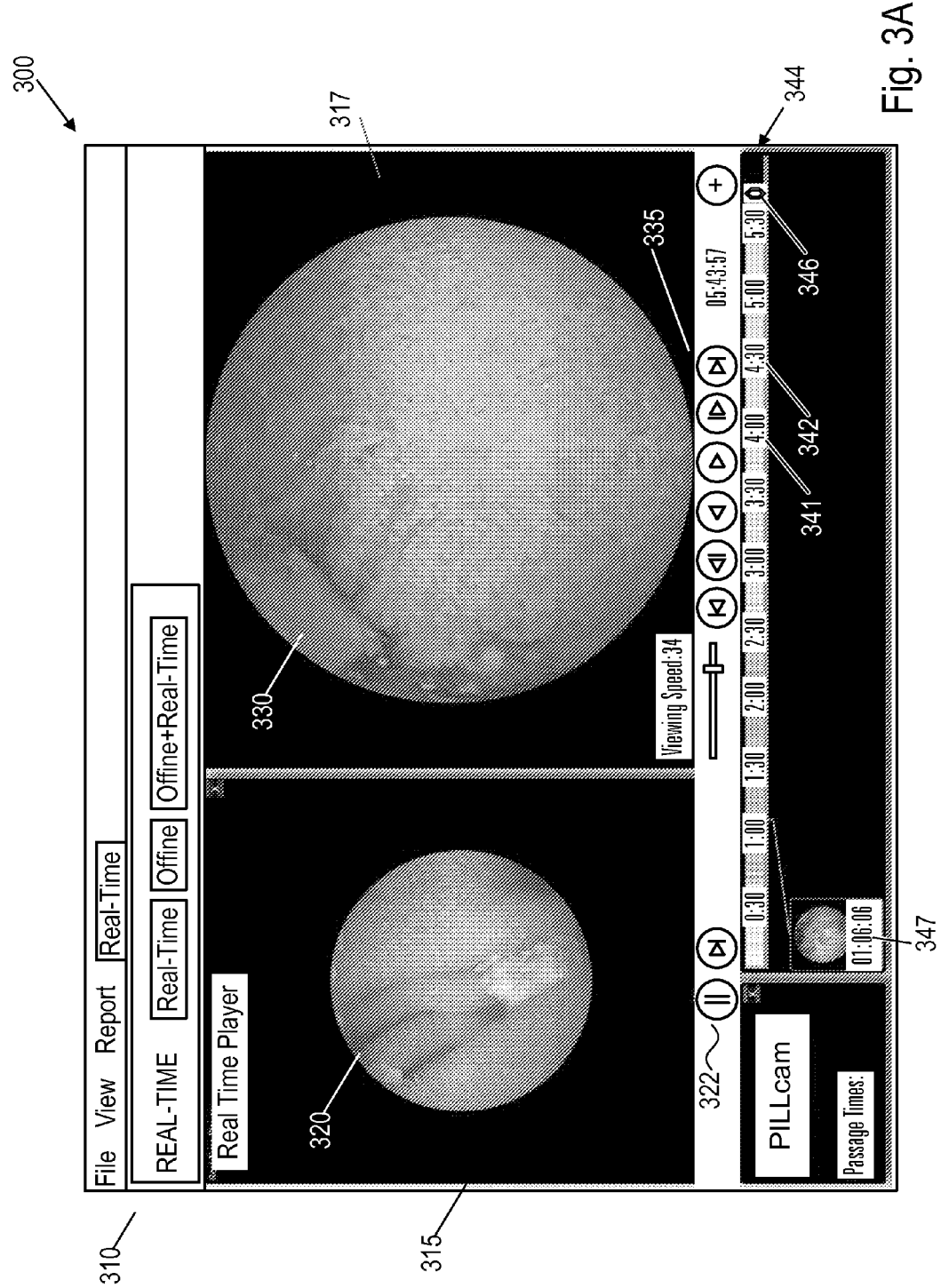
FIGS. 3A-3C illustrate real-time and offline graphic user interfaces for the use of a physician during navigation of an in vivo capsule endoscope according to an example embodiment.

Capsule 40 captures and transmits images as it is maneuvered along the GI tract. The images may be displayed, e.g. in real-time or substantially real-time (e.g. with minimal delay, or delay of fractions of a second) to a user. Reference is now made to FIG. 3A, which is an exemplary graphic user interface of a real-time imaging procedure according to an embodiment of the present invention. Screen 300 may be divided into windows or subareas, which may show one image or multiple images of one or more image streams (e.g. captured by one or more imaging systems). Separate tabs may be used to amalgamate related functionalities, such as File, View, Report and Real-Time tabs. The real-time tab is illustrated in FIG. 3A in detail.

Window 315 shows a real-time streaming display of the images captured by a maneuverable imaging capsule. The real-time display may be generated with minimum delay between the time of capturing the image by the capsule 40 and the time of display of the image on a computer monitor. For example, the delay may be between 1-500 milliseconds, for example 150 milliseconds delay.

The real-time image stream 320 may be paused and restarted using controls 322. In parallel, window 317 shows an offline display of the same image stream. An offline display may be generated after the procedure is terminated, and the user may review the captured images as a video movie. The offline image stream 330 may be played back, stopped, or played using fast-forward and back controls 335. Image stream 330 may be zoomed in or out, and the viewing speed may be adjusted according to the user's preference.

A color or summary bar or summary representation 344 may be generated for the real-time image stream display and displayed in combination with the real time image stream 320 and/or the offline image stream 330. Color bar 344 may include summarized color data of captured in vivo images. In addition to the color information of color bar 344, a time line may indicate the image capture time (measured, for example, from the start of the capsule examination procedure), e.g. 4:00 hours indicated by point 341 and 4:30 hours indicated by point 342. A cursor 346 may mark the position (on the color/time bar) of the currently displayed image within the offline image stream. Generation of the real-time color bar is further described in FIGS. 5A, 5B and 5C.

A color bar may include a number of areas, lines or strips or other components, each summarizing the color of one or more images. The color of each line, strip or other component may, in some embodiments, be an average of colors within an image or across multiple images. Each line, strip or other component may, in some embodiments, include a uniform color or a number of colors which may be arranged in the strip according to a predetermined order. In some embodiments, a single strip may summarize color data extracted from multiple sequential images, or from selected images which were not captured sequentially.

Captured image data may be received and analyzed and processed, e.g. by processor 14, to produce a color bar or summary bar. The processing may include averaging color data values in one or more images, for example computing an arithmetic mean, median, mode or weighted average of color data values from one or more images. For example, a single color strip may be generated for a predetermined number of images (e.g. 100 images) or for a changing number of images. If the color strip is calculated based on a changing number of images, the amount of images used in the calculation may depend on one or more parameters, such as capsule speed, image capturing frame rate of the capsule, and/or similarity between captured images (image similarity may be calculated, for example, for multiple sequential images).

In some embodiments, color data values selected from a portion or a region of the image may be processed, while in other embodiments color data values of all pixels in the image may be used in the analysis and processing. The computed average data values may be presented as color strips in the generated color bar or other summary. The size of a color strip may be, for example one or more pixels in width and several pixel in length.

One or more image thumbnails 347 may be selected and displayed, e.g. along the color/time bar 344. The thumbnails may be captured either offline or in real-time (during the maneuvering procedure), and may be displayed while viewing the offline image stream. For example, a physician guiding the capsule along the GI tract may note suspected pathological regions, or may detect important landmarks (e.g. entrance to the stomach, passage of the capsule to the duodenum or to the cecum, etc.). These images may be captured and stored as thumbnails or other summary images for review, monitoring, diagnosis and reports.

For each frame captured by the capsule, a corresponding orientation and three-dimensional position of the capsule may be obtained (e.g., from the magnetic field sensors, position/location sensors or other positioning sensors) and stored. Thumbnails of selected images may be stored along with their spatial coordinate location. If the physician wishes to direct the capsule to a known position, for example to the spatial coordinates of the last captured thumbnail, MGCE system 100 may allow inputting specific coordinates or a specific landmark image or thumbnail, and may automatically navigate the capsule back to the specified location. A display of the correct direction for maneuvering the capsule may also be provided upon request, for example an arrow pointing to the direction of the requested thumbnail may be displayed relative to the current capsule position.

In box 310 a user may select between a dual combined display which includes offline image stream window 317 and real-time image stream window 315, or a single window display of only real-time or only offline. The combined display may include, in some embodiments, the real time image stream, along with a real time color bar.

Figure 3B:
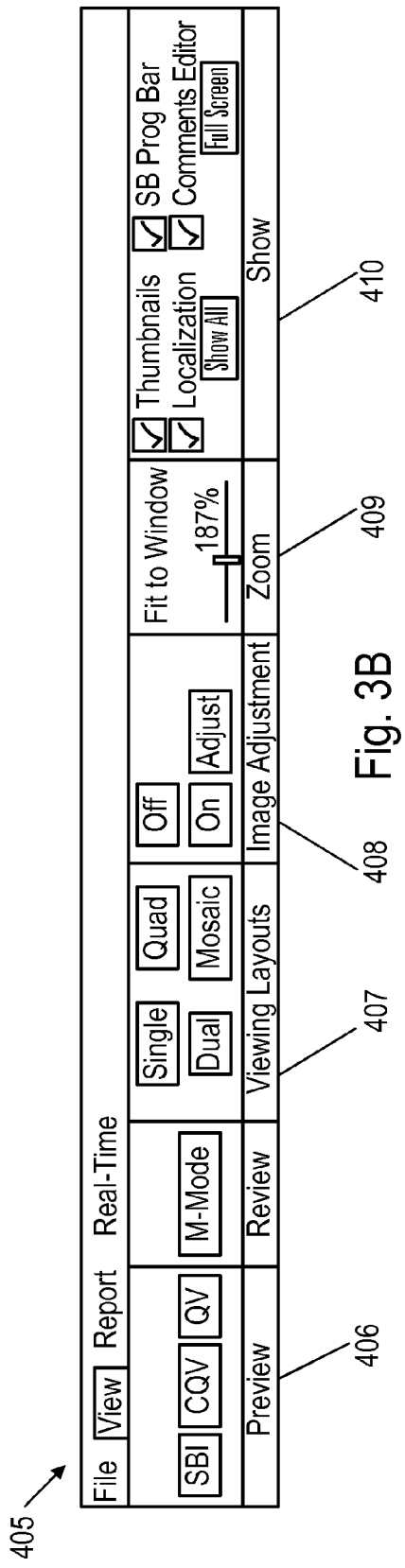

Reference is now made to FIG. 3B, which is an exemplary portion of a graphic user interface for viewing an image stream according to an embodiment of the present invention. The image streams may be displayed as described in FIG. 3A, and a view control tab is illustrated in FIG. 3B in detail. A view control bar 405, which may be positioned for example at the top of the screen, may include controls for adjusting the real-time and offline image stream views.

In some embodiments, not all images captured by the capsule may be presented to the user. For example, images which are captured when the imaging system is close to and pointed at the tissue wall, may be automatically removed or filtered out, and in one embodiment only images showing a view of the lumen hole, e.g. tunnel images or contraction images, may be displayed. Such filtering may assist the physician in maneuvering the capsule, since images which may not be beneficial for providing maneuvering information may be removed from the stream or from display.

Control group 406 includes functions for review and preview of the image streams. Different editing methods may be implemented to generate a filtered or reduced image stream, for example as described in U.S. Pat. No. 7,986,337, and/or in U.S. Patent Application Publication No. 20110243523 to Davidson et al., and/or in U.S. Patent Application No. 20110164126 to Frisch et al., all assigned to the common assignee of the present application and incorporated herein by reference. A reduced image stream including selected images may be streamed or displayed, typically for offline review of a procedure and not in real time, when the user presses the Quick View (QV) control in control group 406. The remaining images, which were not selected in the Quick View reduced stream, may be played when the user selects the CQV (Complementary Quick View) control.

When selecting the manual mode (M-Mode) control, a manual maneuvering scheme may be applied on the capsule, in which the user manually drives the capsule in real-time according to a selected navigation method. In this mode, substantially all images captured by the capsule may be displayed to the user.

In addition to the manual mode, an automatic mode may be activated by the user. The automatic mode may generate a reduced image stream in real time. In order to determine which images are more important (and should be displayed in the reduced stream) and which images can be excluded from the reduced image stream, one or more real-time filters and/or detectors may be activated on each captured image. Real-time filters and detectors may include, for example, pattern recognition and other image processing operations performed on the images, e.g. lumen detector to identify a lumen hole, polyp detector, ulcer detector, blood detector to detect active bleeding, etc. When a user applies the automatic mode, each captured image may be analyzed, e.g. filtered, using a set of fast processing algorithms, and an initial score may be determined for the image. The initial score may be calculated for each image in real-time, without causing substantial delay between the capture time and the display time of the image. According to the initial score, each image may be classified as an "interesting image" (e.g. an image which depicts suspected anomaly or pathological tissue, candidate anatomical landmarks, etc.) or an "uninteresting image". Additional algorithmic processing which may be more time-consuming or resource-consuming may be applied to the images classified as interesting images.

In order to maintain minimal delay between time of image capture to display of the image, in some embodiments, the real-time filters or detectors should process the data very fast, and produce the output while the area under examination is still on display. In order to reduce amount of data for processing, not every image may undergo detection or filtering process. The amount of images which are filtered may depend on the current frame capture rate of capsule 40, and/or on the capsule's current speed. For example, an ulcer detector may be provided to detect an ulcer candidate in an image. The frame rate of the capsule may be 30 frames per second, and the current average speed may be 5 millimeters per second. Considering these parameters, it may be sufficient to execute the ulcer detector on, for example, one out of 50 images, in order to detect ulcer candidates in the imaged tissue. Other ratios of frame selection for detection may be used.

Since processing images in real-time is a substantial task for a processor, different processing pipelines may be generated per disease or per patient type. Certain detectors may be enabled or disabled according to the probability of the pathological occurrence for groups of patients who experience certain symptoms. For example, blood detector may be activated for suspected Crohn's disease patients, while a polyp detector may be disabled. Similarly, a user may select which detectors to activate or de-activate before or during a real-time imaging procedure. In some embodiments, a user may select symptoms from a list of symptoms, e.g. prior to start of the examination, and the system may automatically determine which detectors and filters to activate accordingly.

In some embodiments, different layers of information may be displayed on the monitor. For example, the user may select to view suggested landmarks, pathology candidates, suggested direction (e.g. an indication of a suggested direction) for maneuvering the capsule, etc. Each type of data layer may be displayed or hidden according to the user's preference.

Control group 407 includes several image stream view layouts. The layouts may typically be implemented for review of an offline stream, however, multiple image view layouts are also possible for real-time image stream display. For example, examination procedures may include multiple imaging systems, such as a double-headed imaging capsule, or multiple imaging capsules. Template layouts may include, for example, single image view, dual image view, quad image view (four images are displayed in every time slot), or mosaic image view which may include multiple images arranged in rows and columns.

Image adjustment control group 408 may include different image parameter settings, such as pre-defined and/or user-defined color enhancement, hue, saturation, tone, temperature, brightness, contrast, etc. Zoom control group 409 may include for example a scaling bar for zooming the currently displayed image in and out, and/or a "fit to window" control which may automatically resize the image stream display to the available window size.

Certain windows or portions of the screen may be displayed or hidden according to a user's preference. Control group 410 may include, for example, controls for displaying or hiding thumbnails, location data, comments, etc. The controls may include checkboxes, radio buttons or other known selection methods. Other control buttons and functionalities may be added, and in some embodiments not all controls may be active or available to the user.

Figure 3C:
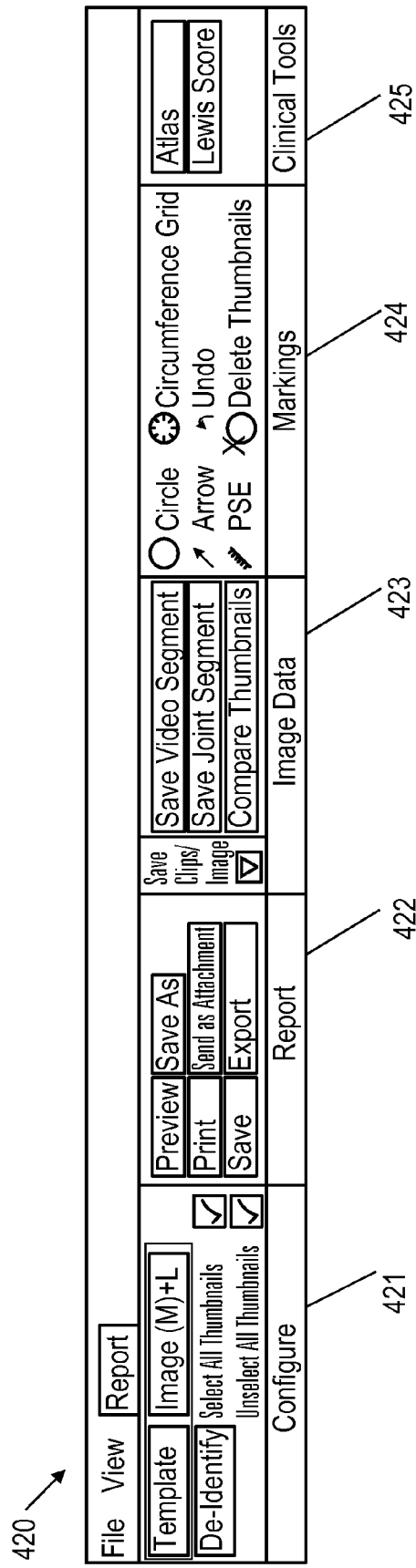

Reference is now made to FIG. 3C, which is an exemplary portion of a graphic user interface for creating reports of an imaging procedure according to an embodiment of the present invention. Example image streams are shown as described in FIG. 3A. An example report control tab is illustrated in FIG. 3C in detail. A control bar, e.g. control bar 420, which may be positioned for example at the top of the screen (e.g. as a separate tab or along with other functionalities), may include controls for creating reports of the imaging procedure. Control group 421 includes configuration functions for preparing the report template. A report template may be selected from a list of predefined templates. The patient's personal details (e.g. identification number, name, etc.) may be hidden or displayed according to the user's selection. The thumbnails which were captured during the examination and/or review procedure may be selected an added to the report.

A report control bar 422 may include document functionalities such as print, print preview, save, send as attachment and export diagnosis or results to other data formats. An image data control bar 423 may include operations on video clips and/or segments of the image stream. Image stream segments or portions may be marked, joined and stored, and selected images (e.g. thumbnails) with different image parameter settings may be compared. Marking control bar 424 may include tools for selecting, marking and measuring features or pathologies in selected images. Arrows, circles, lines or grids may be added to the image for emphasis. A measuring tool or ruler may assist in determining the size of a selected feature or pathology in an image.

A clinical tools box 425 may include tools for assisting a physician during the image stream review or diagnosis process. Clinical tools may include, for example, medical atlas, scoring methods, automatic pathology or anatomical landmark detectors, etc.

An image atlas may include sample images of diseases, pathologies, anatomical landmarks, etc. Scoring methods may be used to assess the condition of the patient. The Lewis score may provide the user with a small bowel image scoring screen which may assist in determining a patient's disease condition. Other tools and functionalities may be added and/or removed from control bar 420.

Reference is made to FIGS. 5A and 5B, which are exemplary color or summary bar representations of a real-time imaging procedure according to an embodiment of the present invention. Color or summary bar representations are described, for example, in U.S. Pat. Nos. 7,636,092 and 8,144,152 to Horn et al., both assigned to the common assignee of the present application and incorporated herein by reference. The color bar representation may include summarized color data from images captured during the procedure. The color bar representation may be displayed as a series of colors that may be at least partially representative of a quantity and/or data collected, e.g. a series of colors where each color presented on the bar may representative of a value of a parameter related to one or more captured images.

Generation of a color bar for a real-time imaging procedure may differ from generation of a color bar for an imaging procedure viewed offline. The presentation of the color bar in an offline imaging procedure is typically calculated based on the image frames which were captured during the procedure, and is a fixed presentation, generated once for the whole image stream. The presentation of a color bar for a real-time imaging procedure may be constantly changing, since new data (e.g., new image data) is continuously or repeatedly accumulated (e.g. received from the capsule) and added to the calculation of the summarized presentation. "New" data or images may include data received after previously received data has been processed and displayed. In some embodiments, each captured image may be added, for example in real time, to the calculation of the average color of the images and may affect the generated color bar. The summarized color bar may typically be based on image data, however, may include other data types such as position and orientation of the capsule or data sensed by other sensors which may be positioned in the capsule or in other components of the system.

Color bar 500 in FIG. 5A is an exemplary color bar continuously or repeatedly generated in real-time according to an embodiment of the invention, to generate an updated summarized color bar. Color bar 500 displays summarized color data strips or areas calculated based on received image data of a real-time imaging procedure. The displayed scale marks 501, 502 provide a time line or an indication about the time that passed since the beginning of the procedure. Time scale marks, labels or indications on a color bar may correlate to the time at which an image frame was captured. A time scale mark indicated on a color strip of the color bar may be correlated to multiple image frames, for example to a group of sequential image frames. A time scale mark for multiple image frames may be computed, for example, as a mean or median of the time of capture of the multiple image frames, or as the time of capture of the first or last image which was used for calculating the color strip color value. The time of capturing of an image frame may be measured from a reference point in time, for example, from the time of beginning of the examination procedure, from time of swallowing the capsule or from the time of activation of the capsule's imaging system. Cursor 546 indicates the capture time of the current image being displayed, e.g. about 3 minutes and 30 seconds in the specific example shown of color bar 500, and indicates the capture time of the last image sent from the capsule and processed for presentation on a computer monitor. The capture time is typically measured since the beginning of the examination procedure, e.g. since the activation of the imaging capsule.

The displayed data length of a real time color bar and the information displayed within a real time color bar may change or may be updated continuously, repeatedly or regularly according to the amount of data which has been accumulated, and according to the time intervals between time scale marks, labels or indications on (or near) the color bar. For example, the length of displayed data in real time color bar 500 is $L_1$, while the length of data in real time color bar 520 is $L_2$. The displayed data length changes in real time as the imaging procedure progresses in time. Additional data (e.g. image data) is received from the capsule, processed and displayed, and the color bar may be continuously or regularly updated. A total maximal length $L_T$ may be allotted for the displayed color bar. The amount of data on color bar 520 may be calculated as the length of the calculated portion of the bar $L_1$, divided by the total maximal length $L_T$.

Time intervals between time scale marks e.g. scale marks 501, 502, 521 and 522 may be determined and updated according to the total time which passed since the beginning of the procedure. For example, during the first few minutes of the procedure, it may be convenient for the user to view scale marks in intervals of, for example, one minute between each mark, as shown in FIG. 5A. However, since a procedure may last a longer time, for example an hour or more, it may be convenient to change the displayed time intervals after a certain time period has elapsed. As an example, FIG. 5B shows an updated color bar 520 generated for a real time imaging procedure which lasts more than three hours. The scale marks 521 and 522 are generated with time intervals of, for example, half an hour between scale marks. As the procedure progresses in time and more images are received, the complete length $L_T$ (which is predetermined as the maximum length allotted for the color bar) may be filled up with summarized color data strips or areas, and the time intervals between scale marks may be updated or may be changed again, for example to intervals of one hour, in order to reduce the length of the displayed data in the color bar and allow addition of summarized color data from newly captured images. Different time intervals between scale marks and different color bar lengths may be used.

In some embodiments, the time scale marks indicated on the displayed color bar may change or be changed or updated periodically, for example at regular intervals of 15 minutes. Other predetermined time intervals may be used. For example, initially (at the beginning of the procedure) the displayed color bar may include time scale marks of for example one-minute intervals, and a total time period of 15 minutes. After 15 minutes, the color bar may be updated or adjusted, and the updated scale marks may indicate intervals of, for example, 2 minutes, and a total of 30 minutes may be shown on the displayed bar. Other intervals and time scales may be used. In another example, the color bar may be updated intermittently, e.g. at irregular intervals, after varying periods of time. For example, a first update may occur 15 minutes after the beginning of the procedure, a second update may occur 15 minutes later (30 minutes after the beginning of the procedure), a third update may occur 30 minutes later (1 hour after the beginning of the procedure) and subsequent changes may occur at 1 hour intervals afterwards.

Figure 5C:
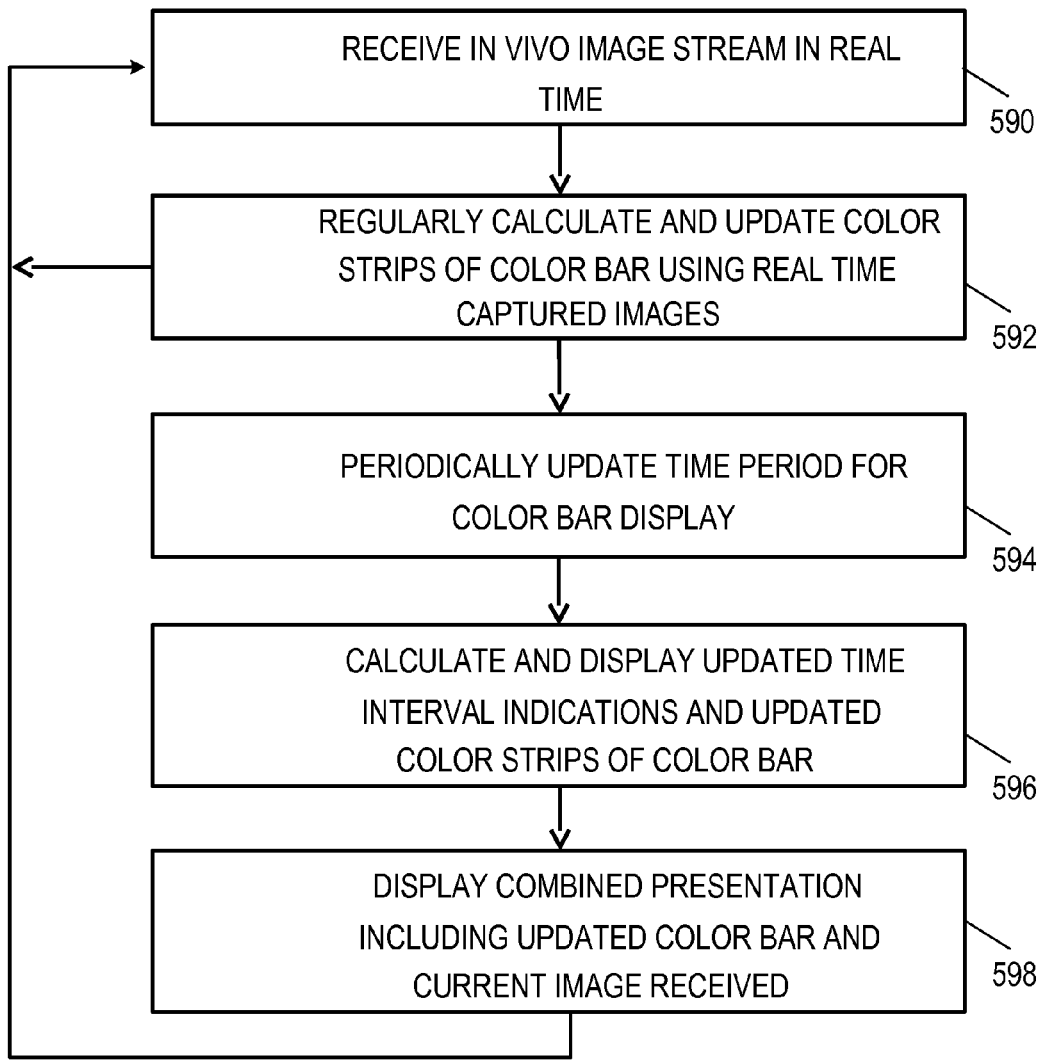
FIG. 5C is a flow chart of a method for displaying an in vivo image stream captured in real time according to embodiments of the present invention.

Reference is now made to FIG. 5C, which is a flow chart of a method for displaying a color bar according to embodiments of the present invention. In operation 590, a stream of in vivo images may be received, for example by a receiver or workstation, in real time during an in vivo imaging procedure. The images may be received for example by a receiver such as data receiver 12, and may be processed by a data processor, e.g. data processor 16 or data processor 14. The data processing of the images may include extracting color data from the images, and calculating or generating summarized color strips or areas (e.g. in operation 592). Each color strip or area may represent an image or a set or sequence of images from the image stream. The summarized color strips may be displayed on the color bar or summary bar, and may be updated regularly or continuously, for example substantially in real time. As the imaging procedure progresses in time, new image data is received, e.g. as images are captured by the imaging device, received by the receiver and processed into summarized color strips, an updated summarized color bar representation with may be generated. As long as the total time period $L_T$ displayed remains fixed during a certain time period of the procedure, the updated color bar may include additional color strips representing the new images received from the imaging device. Upon updating the total time period length $L_T$, the updated color bar may include updated color strips, which may be, for example, reduced in width, in order to adapt the summarized data to the updated total time period $L_T$. Other or different operations may be used.

The total time period length $L_T$ (e.g., shown in FIGS. 5A and 5B) displayed in the color bar and the time scale marks indicated on the displayed color bar may be updated periodically, intermittently or regularly in operation 594. The periodic updates of the displayed time period and time intervals may be in fixed, equal time intervals, e.g. regular updates based on predetermined fixed time periods such as every 10 minutes.

In another embodiment, the periodic updates of the displayed time period and time scale marks may be intermittent, and may be predetermined with changing time periods, for example the initial time period displayed may be 10 minutes, a first update may occur 5 minutes after the beginning of the procedure, a second update may occur 30 minutes after the beginning of the procedure may and a third update may occur 1 hour later. In another embodiment, the periodic updates of the color bar may be determined based on the amount of image data received from the imaging device. For example, a periodic update may occur after a predetermined fixed amount of images are received from the imaging device (e.g. after 1000 images, 10,000 images etc.). In another embodiment, the periodic update of the displayed time period may be triggered or initiated based on the accumulated amount of received image data, e.g. a first update may be triggered after 1000 images are received, a second update may be triggered after 2000 image are received, and a third update may be triggered after 5000 images are received.

In yet another embodiment, the periodic update of the displayed time period may be determined based on a threshold amount of summarized color strips or areas which are displayed on the color bar. For example, if the color strips data fills up a predetermined threshold length, or a predetermined threshold percentage (e.g. 80%) of the displayed time period, a periodic update may be triggered, e.g. automatically by a processing unit such as processor 14.

The time scale marks indicated on the displayed color bar (e.g. time indications 501, 502 on color bar 500) may be automatically determined, e.g. by a processor such as processor 14, according to the total time period length $L_T$ currently on display. Typically, the time scale marks on a color bar will include 5 to 20 intervals, in order to maintain a convenient presentation to the user (e.g., the amount of indications should not be not too dense, using font size which is easy to read).

In some embodiments, following an update of the total time period length displayed, the time scale marks may be calculated, and the color strips or areas may be updated or adapted to match the required resolution of the displayed color bar in operation 596. For example, an update of the total time period length may have occurred at i=25, (i.e. 25 minutes after the beginning of the imaging procedure), when total time period length $L_T$ was, for example, 30 minutes long. At that time, the amount of data displayed in the color bar may be calculated, for example, as $L_i/L_T$ which is 83.3% ($L_i$=25, $L_T$=30). The time scale marks displayed at this time may be include marks of every 5 minutes on the color bar. Each color strip at this time may represent, for example, 5 images from the captured image stream. After the total time period length $L_T$ is updated to, for example, 60 minutes, the color strips' resolution is reduced in order to fit the updated time scale marks. When i=26 (i.e., 26 minutes after the beginning of the procedure), the amount of data on the color bar is 26/60 or 43.3%. Thus, each color strip at this point of time in the real-time imaging procedure may represent, for example, 10 images from the image stream. The color bar may be continuously filled up with, or have added to it, additional color strips as more or new images are received from the imaging device.

In operation 598, an updated color bar may be displayed, combined with the image stream received in real time. For example, e.g. as shown in FIG. 3A, an updated color bar representation may include updated color strips, which are added as new images are received from the imaging device and processed into summarized color data. The updated color bar representation may also include updated time scale marks, which are adapted to the amount of information which is displayed on the color bar. The combined representation may include the current real time image received from the imaging device (e.g. from image stream 320), or the real-time image data. In some embodiments, the presentation may also include an offline image stream view, e.g. from image stream 330 shown in FIG. 3A.

Figure 6:
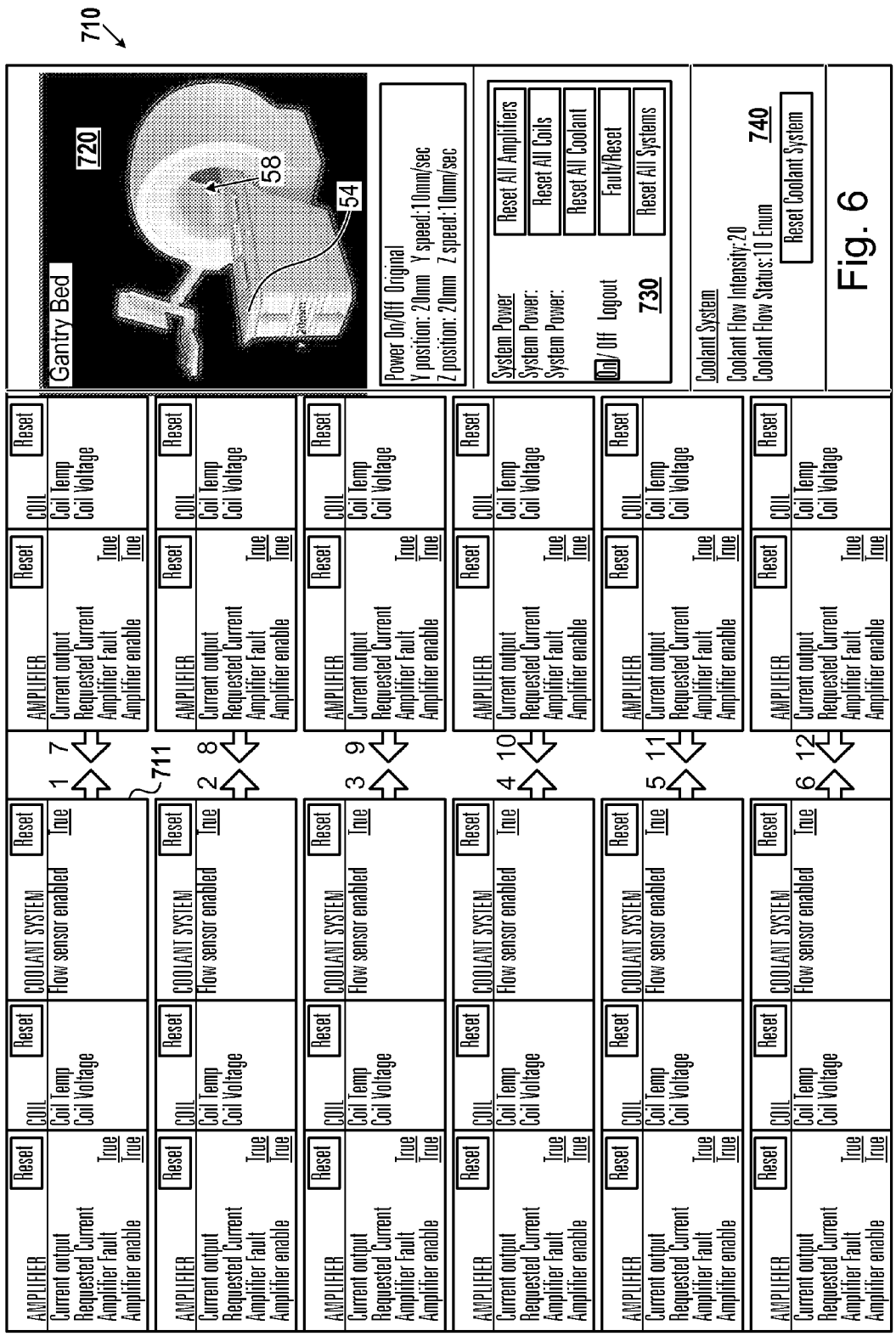
FIG. 6 illustrates a graphic user interface for configuring magnetic system parameters during a magnetically guided capsule procedure according to an example embodiment.

Reference is made to FIG. 6, which illustrates a graphic user interface for configuring and monitoring parameters of a system for magnetically guiding an in vivo capsule according to an example embodiment. Different parameters may be arranged in several windows on the display screen, e.g. windows 710-740. In window 710, sets of parameters for controlling coils 60, amplifiers, cooling system and other components of the magnetic maneuvering system 100 are shown. The parameters may be arranged in display window 710 according to the physical coils of system 100, e.g. 12 coils may be numbered 1-12. For each coil and amplifier, control parameters may be configured in a control box, e.g. control box 711 which controls coil #2. Examples of control and monitoring parameters may include (but are not limited to): current output (which indicates an output current of the coil), requested current (which controls an input current according to the user indication), amplifier fault indication, amplifier enablement indication, coil temperature (which monitors the temperature of the activated coil), coil voltage (which indicates the voltage of the activated coil) and coolant system flow sensor indication.

Window 720 includes a schematic illustration of gantry 70 which may include, for example, diagnosis chamber 50, carriage 54, coils 60, and MDCC 20. The position and speed of carriage 54 may be configurable or monitored by the user, e.g. according to Y axis and Z axis coordinates shown in window 720.

In some embodiments, position and speed of carriage 54 may be set automatically according to predefined parameters. An exemplary parameter may include the local magnetic forces working on the capsule. The magnetic forces may be distributed unevenly throughout magnetic maneuvering space 58. For example, the external magnetic forces driving the capsule may be stronger in the middle of maneuvering space 58 and weaker at the outskirts or periphery. Accordingly, a model of the magnetic maneuvering forces may be calculated for maneuvering space 58 and carriage 54 may be glided to a position which maximizes the magnetic forces working on the capsule. Such automatic setting of carriage 54 may increase accuracy of the navigation procedure.

In window 730 the system may be reset, for example per component (amplifiers, coils, coolant system, etc.) or fully (reset all system hardware and software components). The coolant flow intensity and status may be monitored in window 740. Other components may be monitored and configured through different windows or control boxes.

It is noted that while embodiments of the invention described herein are adapted for imaging of the GI tract, the devices and methods disclosed herein may be adapted for imaging other body cavities or spaces.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for displaying an in vivo imaging capsule procedure, the method comprising:
receiving real-time image data captured by the capsule during an in-vivo procedure;
generating a summarized color bar, said color bar comprising color strips and time scale marks, said color strips generated based on color values of image data as new image data is received, wherein the summarized color bar has a total maximal length $L_T$ allotted for the summarized color bar;
updating said color strips, as new image data is received, by adding color strips representing new images received;
if the total maximal length $L_T$ of the summarized color bar is filled with color strips:
  reducing a resolution of said color strips,
  updating a total time period represented by the total maximal length $L_T$, and
  updating a time interval between said time scale marks according to a time passing from the beginning of the in-vivo procedure;
updating the summarized color bar according to one or more of: any updated time interval between the time scale marks and any updated color strips; and
displaying a combined display comprising the summarized color bar and an image stream, the image stream comprising the real-time image data.

2. The method according to claim 1 comprising:
receiving real-time location data of the capsule, the location data indicating a position and orientation of the capsule in vivo;
analyzing the location data and image data in real-time to determine a suggested direction for maneuvering the capsule; and
displaying, on a current image displayed from the image stream, an indication of the suggested direction.

3. The method according to claim 1 wherein the updates to the time interval are based on predetermined fixed time intervals.

4. The method according to claim 1 wherein the updates to the time interval are based on varying time intervals.

5. The method according to claim 1 wherein the updates to the time interval depend on an amount of received image data.

6. The method according to claim 1 wherein updating sad color strips is triggered based on the amount of received image data.

7. The method according to claim 1, wherein updating color strips comprises adding color strips to the color bar.

8. The method according to claim 1, wherein updating color strips comprises representing additional images by each color strip.

9. The method according to claim 1, comprising updating the time interval based on the amount of received image data or a time elapsing from a beginning of the in-vivo imaging.

10. The method according to claim 1, wherein updating a time interval between time scale marks comprises increasing the time interval.

11. A system for displaying a real time in vivo imaging procedure, the system comprising:
- a receiver for receiving real-time image data captured by an in vivo imaging device during an in-vivo procedure;
- a processor to:
  - generate a summarized color bar, said color bar comprising color strips and time scale marks, said color strips based on color values of image data as new image data is received, wherein the summarized color bar has a total maximal length $L_T$ allotted to the summarized color bar;
  - update said color strips, as new image data is received, by adding color strips representing new images received;
  - if the total maximal length $L_T$ of the summarized color bar is filled with color strips:
    - reduce a resolution of said color strips,
    - update a total time period represented by the total maximal length $L_T$, and
    - update a time interval between said time scale marks according to a time passing from the beginning of the in-vivo procedure; and
  - update the summarized color bar according to one or more of: any
  - updated time interval between the time scale marks and updated color strips; and
- a display for displaying a combined display comprising the summarized color bar and an image stream, the image stream comprising the real-time image data.

12. The system according to claim 11 wherein the receiver is to receive real-time location data of the capsule, the location data indicating a position and orientation of the capsule in vivo, and wherein the processor is to analyze the location data and image data in real-time to determine a suggested direction for maneuvering the capsule and to display the suggested direction on a current image displayed from the image stream.

13. The system according to claim 11 wherein the updates to the time interval are based on predetermined fixed time intervals.

14. The system according to claim 11 wherein the updates to the time interval are based on varying time intervals.

15. The system according to claim 11 wherein the updates to the time interval depend on an amount of received image data.

16. The system according to claim 11 wherein the update to said color strips is triggered based on an amount of received image data.

17. A method for displaying in vivo imaging capsule information, the method comprising:
- receiving image data captured by the capsule;
- repeatedly generating an updated summary bar, said summary bar including color areas and time scale marks having time intervals between the time scale marks, said summary bar calculated based on color values of received image data, wherein said summary bar is updated as new image data is received, wherein the summary bar has a total maximal length $L_T$ allotted for the summary bar;
- updating said color areas, as new image data is received, by adding color areas representing new images received;
- if the total maximal length $L_T$ of the summary bar is filled with color areas:
  - reducing a resolution of said color areas,
  - updating a total time period represented by the total maximal length $L_T$, and
  - updating the time intervals between said time scale marks;
- calculating an updated summary bar according to either of the updated time interval between the time scale marks and updated color areas; and
- displaying the summary bar and an image stream, the image stream comprising the real-time image data.

18. The method according to claim 17 comprising:
- receiving real-time location data of the capsule, the location data indicating a position and orientation of the capsule in vivo; and
- analyzing the location data and image data in real-time to determine a suggested direction for maneuvering the capsule.

* * * * *